United States Patent
Kusanagi et al.

(10) Patent No.: US 11,547,361 B2
(45) Date of Patent: Jan. 10, 2023

(54) DISPLAY CONTROLLER, DISPLAY DEVICE, DISPLAY SYSTEM, MOBILE OBJECT, IMAGE GENERATION METHOD, AND CARRIER MEANS

(71) Applicant: Ricoh Company, Ltd., Tokyo (JP)

(72) Inventors: Masato Kusanagi, Kanagawa (JP); Hiroshi Yamaguchi, London (GB); Yuuki Suzuki, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 17/419,005

(22) PCT Filed: Dec. 20, 2019

(86) PCT No.: PCT/JP2019/050138
§ 371 (c)(1),
(2) Date: Jun. 28, 2021

(87) PCT Pub. No.: WO2020/145093
PCT Pub. Date: Jul. 16, 2020

(65) Prior Publication Data
US 2021/0393206 A1    Dec. 23, 2021

(30) Foreign Application Priority Data
Jan. 11, 2019   (JP) .............................. JP2019-003693

(51) Int. Cl.
*A61B 5/00*    (2006.01)
*B60K 35/00*   (2006.01)
(Continued)

(52) U.S. Cl.
CPC ............ *A61B 5/6893* (2013.01); *B60K 35/00* (2013.01); *G02B 27/0101* (2013.01); *G06F 3/14* (2013.01);
(Continued)

(58) Field of Classification Search
CPC ........ A61B 5/6893; A61B 5/18; B60K 35/00; B60K 2370/1529; B60K 2370/166;
(Continued)

(56) References Cited

U.S. PATENT DOCUMENTS

2004/0044291 A1* 3/2004 Yasushi .................... A61B 5/18
                                                                600/509
2016/0167514 A1    6/2016 Nishizaki et al.
(Continued)

FOREIGN PATENT DOCUMENTS

EP    3 428 033 A1    1/2019
JP    2002-25000 A    1/2002
(Continued)

OTHER PUBLICATIONS

International Search Report and Written Opinion dated Apr. 30, 2020 in PCT/JP2019/050138 filed on Dec. 20, 2019.
(Continued)

*Primary Examiner* — Brent D Castiaux
(74) *Attorney, Agent, or Firm* — Xsensus LLP

(57) ABSTRACT

A display controller (20) includes an information acquisition unit configured to obtain input data of attentional resources of an occupant of a mobile object such as traveling time, occupant status information, driving environment information or display image history and a display-image generation unit configured to generate, in a mode determined based on the input data, a display image to be displayed by a display
(Continued)

device (10) provided for the mobile object. The mobile object is for instance a vehicle comprising a head-up display.

18 Claims, 34 Drawing Sheets

(51) Int. Cl.
*G02B 27/01* (2006.01)
*G06F 3/14* (2006.01)
*G09G 3/00* (2006.01)
*A61B 5/18* (2006.01)

(52) U.S. Cl.
CPC ............... *G09G 3/002* (2013.01); *A61B 5/18* (2013.01); *B60K 2370/1529* (2019.05); *B60K 2370/166* (2019.05); *B60K 2370/167* (2019.05); *B60K 2370/169* (2019.05); *B60K 2370/178* (2019.05); *B60K 2370/1868* (2019.05); *B60K 2370/1876* (2019.05); *B60K 2370/52* (2019.05); *G02B 2027/014* (2013.01); *G02B 2027/0141* (2013.01); *G09G 2354/00* (2013.01); *G09G 2380/10* (2013.01)

(58) Field of Classification Search
CPC ........ B60K 2370/167; B60K 2370/169; B60K 2370/178; B60K 2370/1868; B60K 2370/1876; B60K 2370/52; G02B 27/0101; G02B 2027/014; G02B 2027/0141; G06F 3/14; G09G 3/002; G09G 2354/00; G09G 2380/10
See application file for complete search history.

(56) References Cited

U.S. PATENT DOCUMENTS

| | | |
|---|---|---|
| 2016/0203590 A1 | 7/2016 | Mochizuki |
| 2017/0001522 A1 | 1/2017 | Mochizuki et al. |
| 2017/0230628 A1 | 8/2017 | Ichikawa et al. |
| 2017/0336629 A1 | 11/2017 | Suzuki et al. |
| 2018/0009442 A1* | 1/2018 | Spasojevic ............. B60K 28/02 |
| 2018/0180879 A1* | 6/2018 | Yamaguchi ............ G06V 20/56 |
| 2018/0218711 A1 | 8/2018 | Suzuki et al. |
| 2018/0319281 A1* | 11/2018 | Nishizaki ............. G02B 26/105 |
| 2018/0339591 A1 | 11/2018 | Suzuki et al. |

FOREIGN PATENT DOCUMENTS

| | | | |
|---|---|---|---|
| JP | 2003-317197 A | | 11/2003 |
| JP | 2010-079844 A | | 4/2010 |
| JP | 2016-179709 A | | 10/2016 |
| JP | 2016179709 A | * | 10/2016 |
| JP | 2017-068761 A | | 4/2017 |
| JP | 2017068761 A | * | 4/2017 |
| JP | 2017068761 A | * | 4/2017 |
| JP | 2017-90996 A | | 5/2017 |
| JP | 2017-211366 A | | 11/2017 |
| WO | WO 2017/155199 A1 | | 9/2017 |

OTHER PUBLICATIONS

Japanese Office Action dated Jul. 12, 2022, in corresponding Japanese Application No. 2019-003693.

* cited by examiner

WATCH THE LINE —303b

DISPLAY CONTROLLER, DISPLAY DEVICE, DISPLAY SYSTEM, MOBILE OBJECT, IMAGE GENERATION METHOD, AND CARRIER MEANS

TECHNICAL FIELD

Embodiments of the present disclosure relates to a display controller, a display device, a display system, a mobile object, an image generation method, and a carrier means.

BACKGROUND ART

Vehicle-installed display devices are known in the art that display various kinds of vehicle-related information that can be obtained from a vehicle such as the vehicle speed, the remaining fuel, the operative position of a shift lever, the total mileage, the sectional mileage, the state of a direction indicator, and the water temperature, and provide such various kinds of vehicle-related information to the occupant of a mobile object such as a driver. The occupant of the vehicle as an example of the mobile object can check such various kinds of vehicle-related information at any time even while he or she is driving the vehicle.

Currently, an advanced driver assistance system (ADAS) that assists the driving operation of a vehicle is in common use. For example, various kinds of sensors such as a light detection and ranging (LiDAR) device and a camera are installed in a vehicle. The display device displays, for example, the data detected by a sensor, the status of various kinds of controls that is determined based on the data obtained by the sensor, and the desirable operations performed by the occupant of the vehicle. Accordingly, the occupant of the vehicle can check the control state or perform driving operation upon viewing such kinds of information.

Moreover, the display device can display the information obtained from an external device. For example, the traffic congestion information that is received by a vehicle information communication system (VICS, registered trademark) receiver or accident information can be displayed by the display device.

Further, a system is becoming commercialized in which occupant status information is detected from the occupant of the vehicle to estimate, for example, the physical and mental state of the occupant of the vehicle and a display device displays, for example, information encouraging to take a rest. Moreover, technologies are known in the art to change the way of presenting the information about the vehicle depending on the physical and mental state of the occupant of the vehicle (see, for example, PTL 1). PTL 1 discloses an information presenting device that presents the physical and mental state of the driver in an easy-to-understand format by changing the way of presenting the icon of the vehicle according to the live-subject information of the driver.

CITATION LIST

Patent Literature

PTL 1: Japanese Patent Application Publication No. 2017-068761

SUMMARY OF INVENTION

Technical Problem

However, in the known technologies, information cannot be displayed based on the attentional resources of the occupant of the vehicle. The occupant of the vehicle allocates the amount of attentional resources at that moment in time between the driving operation and the visual recognition of the information displayed by the display device, but it is known in the art that the attentional resources vary depending on the traveling time, the occupant status information, the driving environment information, or the display image history. These kinds of information may include, for example, the data that correlates with the degree of fatigue, and the attentional resources may vary depending on the degree of fatigue.

Moreover, it is known in the art that, when cases in which the information with good visual recognizability is displayed are compared with cases in which the information with poor visual recognizability is displayed, the amount of attentional resources that can be allocated to driving operation decreases when the information with poor visual recognizability is displayed. In view of the above circumstances, when the information that can visually be recognized with a small amount of attentional resources is displayed, the amount of attentional resources that can be allocated to the driving operation increases. However, in the related art, information is not displayed based on the attentional resources of the occupant of a vehicle.

Solution to Problem

A display controller includes an information acquisition unit configured to obtain input data of attentional resources of an occupant of a mobile object, and a display-image generation unit configured to generate, in a mode determined based on the input data, a display image to be displayed by a display device provided for the mobile object.

Advantageous Effects of Invention

According to one aspect of the present disclosure, a display controller by which information is displayed based on the attentional resources of the occupant of a vehicle can be provided.

BRIEF DESCRIPTION OF DRAWINGS

The accompanying drawings are intended to depict example embodiments of the present invention and should not be interpreted to limit the scope thereof. The accompanying drawings are not to be considered as drawn to scale unless explicitly noted. Also, identical or similar reference numerals designate identical or similar components throughout the several views.

FIG. 9A-1, FIG. 9A-2, FIG. 9B-1, FIG. 9B-2, FIG. 9C-1, and FIG. 9C-2 are diagrams each illustrating a change in display mode where the size or thickness of text or character and the brightness are changed and complementary colors are used, according to an embodiment of the present disclosure.

FIG. 10A-1, FIG. 10A-2, FIG. 10B-1, FIG. 10B-2, FIG. 10C-1, and FIG. 10C-2 are diagrams each illustrating a change in display mode where the level of color saturation or the distance to a virtual image is changed, or flashing is used, according to an embodiment of the present disclosure.

DESCRIPTION OF EMBODIMENTS

Embodiments of the present disclosure are described below with reference to the accompanying drawings. In particular, a display system and a method of generating an image using the display system are described.

Firstly, a schematic configuration of a method of generating the image of information according to an embodiment of the present disclosure is described with reference to FIG. 1.

Figure 1:
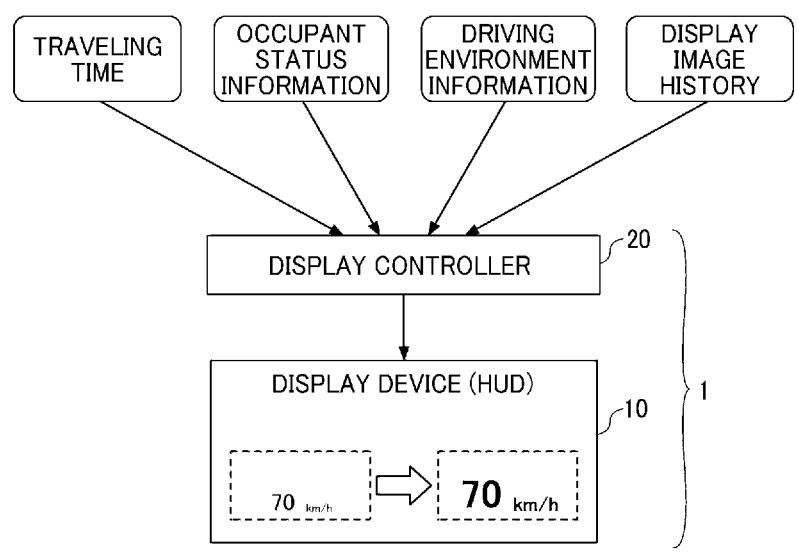
FIG. 1 is a diagram illustrating the display mode of the information displayed by a display device, which is determined by a display controller depending on the attentional resources of the occupant of a vehicle, according to an embodiment of the present disclosure.

FIG. 1 is a diagram illustrating the display mode of the information displayed by a display device 10, which is determined by a display controller 20 depending on the attentional resources of the occupant of a vehicle, according to the present embodiment.

In the present embodiment, cases in which the display controller 20 displays the information using a heads-up display (HUD) as the display device 10 are described. However, no limitation is intended thereby, and the display device 10 may be other various kinds of display devices such as a liquid crystal display (LCD).

It is assumed that the display controller 20 is provided for a mobile object such as a vehicle, and at least one of the traveling time (that may also be referred to as driving time in the following description), the occupant status information such as the heart rate, the driving environment information such as the control state of an object, and the display image history of various kinds of information displayed by the display device 10 (all of or some of these elements of information may be referred to as input data in the following description) is input to the display controller 20 from a sensor provided for the vehicle.

The input data is information that may affect the attentional resources of the occupant of a vehicle, and some of the input data is correlated with a physical and mental state such as a level of fatigue.

The display controller 20 determines the display mode of the display image to be displayed by the display device 10 based on the input data.

For example, when the traveling time reaches or exceeds a certain level, in FIG. 1, the information "70 kilometers (km)/hour (h)", which is the current vehicle speed, is displayed with a greater size so as to be visually recognized with a smaller amount of attentional resources.

As described above, the display device 10 according to the present embodiment determines the display mode of the information so as to be visually recognized with a smaller amount of attentional resources, depending on the input data that may affect the attentional resources of the occupant of the vehicle. Accordingly, the occupant of the vehicle can visually recognize the information easily, and can easily secure the attentional resources that can be allocated to the driving operation. Moreover, as the information can be visually recognized with a smaller amount of attentional resources, the accumulation of fatigue can be eased.

The term "attentional resources" are the resources that are used when the brain is active. When some of the attentional resources is assigned to a task A, a task B has to be dealt with the remaining attentional resources. The total amount of attentional resources that the occupant has decreases due to the fatigue. The occupant of the vehicle allocates his/her total amount of attentional resources between the driving operation and the visual recognition of the information. The ratio of the allocation varies depending on the conditions.

In a display mode where information can visually be recognized with a smaller amount of attentional resources, for example, the degree of stimulation is increased or the image of the information is highlighted. Whereas information with good visibility can visually be recognized with a smaller amount of attentional resources, information with poor visibility requires a greater amount of attentional resources to visually recognize the image of the information.

The input data is the data that is input to the display controller 20 and is related to the attentional resources of the occupant of a mobile object in some way. For example, the input data may decrease or increase the attentional resources of the occupant of the mobile object. In the present embodiment, the traveling time, the occupant status information such as the heart rate, the driving environment information such as the control state of an object, and the display image history of various kinds of information displayed by the display device 10 are used as an example of the input data. Some of or all of the input data is used as the display data in the display system 1, which is displayed by the display device 10.

The occupant of the vehicle indicates a person who visually recognizes the information displayed by the display device 10. For example, the occupant is a driver. However, the occupant may simply be an occupant. In the case of a mobile object that travels by automatic driving, the occupant may not at all drive the mobile object.

The term "mobile object" is satisfactory as long as at least one occupant rides on the mobile object and the mobile object travels on the ground, in the air, on the sea, or in the sea. In the present embodiment, cases in which the mobile object is a vehicle are described. For example, the display device 10 may be provided for an aircraft, ship, and an industrial robot.

The term "display data" indicates the data that is displayed by the display device 10, and the term "display image" indicates the image data based on the display data. The display image is generated based on at least one item of display data. The term "contents of data" indicates items of display data that are included in the display image.

The display data that is displayed by the display device 10 includes the vehicle-related information, the driving environment information, the occupant status information, and the information that is derived from those items of information. Qualitatively, the display data that is displayed by the display device 10 is useful information for driving the mobile object. Whether the information is actually reflected in driving does not matter in the present embodiment. Concrete examples of those items of information in the present embodiment are given below, but no limitation is intended thereby.

Vehicle-related Information: Various kinds of information that can be obtained from a vehicle such as the vehicle speed, the remaining fuel, the operative position of a shift lever, the total mileage, the sectional mileage, the state of a direction indicator, and, the water temperature.

Driving Environment Information: Various kinds of information such as the status of various kinds of controls based on the information detected by various kinds of sensors such as a light detection and ranging (LiDAR) device and a camera, the desirable operations performed by the occupant of the vehicle, the traffic congestion information received by a vehicle information communication system (VICS, registered trademark) receiver, the information about traffic accident, the environmental information related to driving such as the weather information. Moreover, for example, the information about the directions of travel and the traffic signs, which is supplied by a navigation system, may be included in the driving environment information.

Occupant Status Information: Various kinds of information such as the electrocardiogram information of the occupant of the vehicle, the heart rate, the blood pressure, the body temperature, the beat of the pulse, the respiration rate, the amount of perspiration, the level of blinking or pupil (arousal level), the electrical brain waves, and the myoelectric potential, or the information about the physical and mental state determined based on these items of information.

Figure 2:
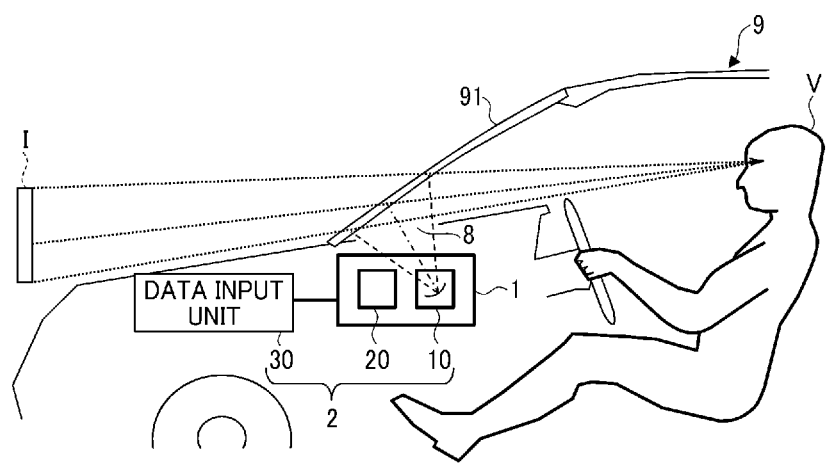
FIG. 2 is a diagram illustrating a schematic configuration of a vehicle-installed system according to an embodiment of the present disclosure.

FIG. 2 is a schematic diagram illustrating a vehicle-installed system 2 according to an embodiment of the present disclosure.

The vehicle-installed system 2 is provided for a vehicle 9, and includes data input unit 30 and the display system 1. Further, the display system 1 includes a display controller 20 and a display device 10. Firstly, the data input unit 30 obtains the above input data and sends the obtained input data to the display system 1, as will be described later in detail.

The display system 1 is embedded in the dashboard, and projects an image towards a front windshield 91 through an exit window 8 arranged on the top surface of the display system 1. The projected image is displayed ahead of the front windshield 91 as a virtual image I. The occupant V of the vehicle can visually check useful information for driving with a smaller amount of line-of-sight movement while keeping the line of sight on the preceding vehicle or the road surface. The display system 1 is satisfactory as long as it can project an image towards the front windshield 91, and may be placed on, for example, the ceiling panel or a sun visor of the vehicle, in place of the dashboard.

The display system 1 may be a general-purpose information processing terminal or a HUD-dedicated terminal. The HUD-dedicated terminal may be referred to simply as a heads-up display, or may be referred to as a navigation system when the HUD-dedicated terminal is integrated into a navigation system. Alternatively, the HUD-dedicated terminal may be referred to as a portable navigation device (PND), a display audio, or a connected audio. When the HUD-dedicated terminal is referred to as a display audio, such a device does not provide navigation functions but provides, for example, audio video functions and communication capability.

A general-purpose information processing terminals may be, for example, a smartphone, a tablet personal computer (PC), a mobile phone, a personal digital assistance (PDA), a laptop PC, a wearable PC (e.g., a wristwatch-type wearable PC and a sunglass-type wearable PC). However, no limitation is intended thereby, and a general-purpose information processing terminal is satisfactory as long as it has the general functions of information processing devices. A general-purpose information processing terminal is usually used as an information processing apparatus that executes various kinds of applications. However, for example, when application software for the display system is to be executed, a general-purpose information processing terminal displays useful information for driving in a similar manner to a HUD-dedicated terminal.

The display system 1 according to the present embodiment may be switchable between a vehicle-installed state and a portable state regardless of whether the display system 1 is a general-purpose information processing terminal or a HUD-dedicated terminal.

As illustrated in FIG. 2, the display system 1 includes the display device 10 and the display controller 20 as elements. The display device 10 according to the present embodiment may adopt the laser scanning system or the panel system as known in the art, as its projection system. In the laser scanning system, an intermediate image (i.e., a real image projected onto a screen as will be described later in detail) is formed by scanning a laser beam emitted from a laser beam source, using a two-dimensional scanning device. In the panel system, an intermediate image is formed by an imaging device such as a liquid crystal panel, a digital micromirror device (DMD) panel (digital mirror device panel), and a vacuum fluorescent display (VFD).

Unlike the panel system where an image is formed by partial light blocking over the full-screen emission, the laser scanning system is preferable because emitting/non-emitting can be assigned to each pixel and a high-contrast image can be formed in most cases. When a high-contrast image can be obtained, the viewability increases. Accordingly, in the laser scanning system, the occupant of a vehicle can visually recognize the information with smaller attentional resources than the attentional resources required when a HUD of the panel system is adopted.

In particular, in the panel system, the light that cannot be shielded is projected even to an area with no information, and an unwanted frame tends to be projected to a range where the HUD can display an image (this phenomenon may be referred to as a postcard effect). By contrast, no such phenomenon is observed in the laser scanning system, and only the image of contents of data can be projected in the laser scanning system. In particular, the reality improves when the image of generated video data is superimposed on the existing scenery in the augmented reality (AR). The augmented reality (AR) is the technologies for virtually expanding the real-world environment by overlaying the image of an unreal object on the existing scenery. However, no limitation is indicated thereby, and a HUD of the panel system is satisfactory as long as it can display the image of information in a mode where the occupant of the vehicle can visually recognize the image of information with a smaller amount of attentional resources.

Figure 3:
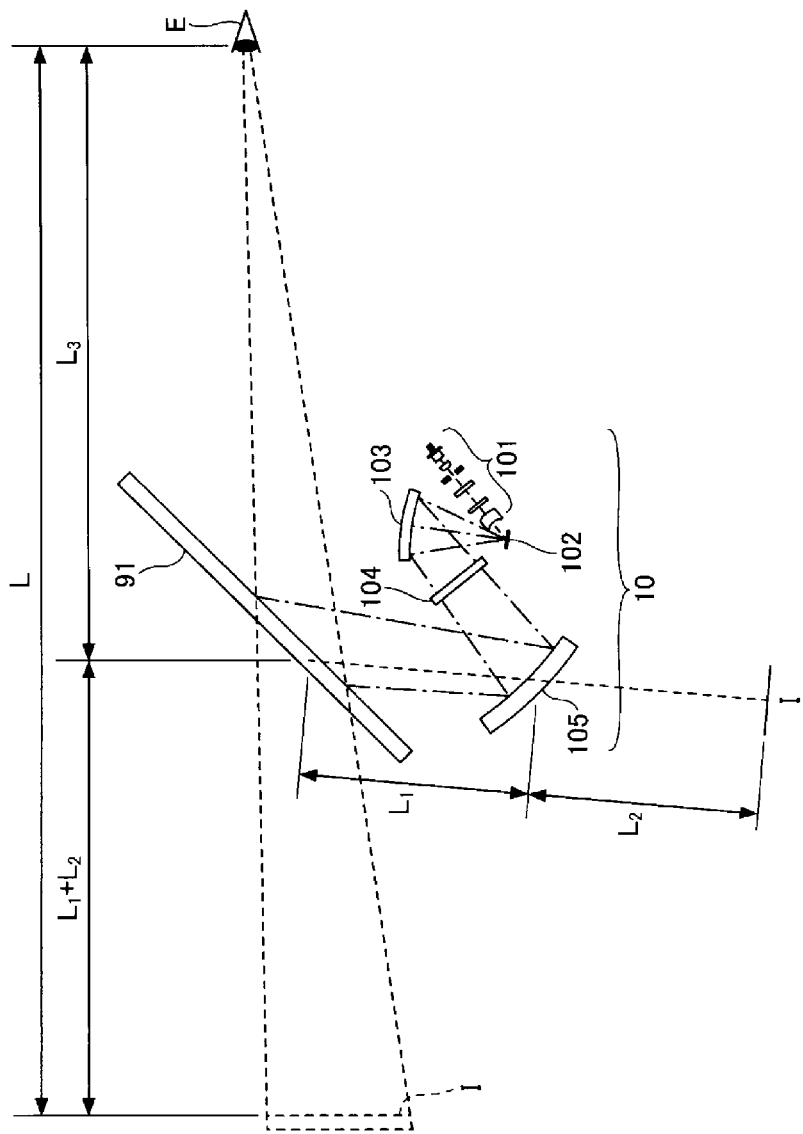
FIG. 3 is a diagram illustrating a configuration of a display device according to an embodiment of the present disclosure.

FIG. 3 is a diagram illustrating a configuration of the display device 10 according to the present embodiment.

The display device 10 includes a light source unit 101, a light deflector 102, a mirror 103, a screen 104, and a concave mirror 105. However, no limitation is indicated thereby, and the display device 10 may include other elements not illustrated in FIG. 3. Moreover, it is not necessary for the display device 10 to include all the elements illustrated in FIG. 3.

The light source unit 101 includes, for example, three laser beam sources that correspond to red, green, and blue (RGB) (each of which is referred to as a laser diode (LD) in the following description), coupling lenses, apertures, combiners, and lenses, and the laser beams that are emitted from the three LDs are combined and guided and directed to the reflection plane of the light deflector 102. The laser beams that are guided to the reflection plane of the light deflector 102 are two-dimensionally deflected by the light deflector 102.

For example, one micromirror that pivots around the two axes that are perpendicular to each other or two micromirrors that pivots around or rotate on one axis may be used as the light deflector 102. For example, the light deflector 102 may be a micro-electromechanical systems (MEMS) mirror that is manufactured by any process such as the semiconductor processing. For example, the light deflector 102 may be driven by an actuator whose driving force is the deforming force of a piezoelectric element. As the light deflector 102, for example, a galvano mirror or a polygon mirror may be used.

The laser beams that are two-dimensionally deflected by the light deflector 102 are incident on the mirror 103, and are reflected and turned by the mirror 103. As a result, a two-dimensional image (intermediate image) is drawn on the surface (to-be-scanned surface) of the screen 104. For example, a concave mirror can be used as the mirror 103. Alternatively, a convex mirror or plane mirror may be used as the mirror 103. The display device 10 can be downsized or the arrangement of the elements can flexibly be changed by deflecting the laser beams by the light deflector 102 and the mirror 103 to change the directions of the laser beams.

As the screen 104, it is preferable to use a microlens array (MLA) or a micromirror array through which laser beams diverge at a desired divergence angle. However, no limitation is indicated thereby, and a diffuser panel through which laser beams diffuse at a desired divergence angle, a transparent plate or reflector whose surfaces are smooth, or the like may be used.

The laser beams that are emitted from the screen 104 are reflected by the concave mirror 105, and are projected onto the front windshield 91. The concave mirror 105 has a function similar to lenses and has the function of forming an image at a predetermined focal length. Accordingly, assuming that the concave mirror 105 serves as a lens, an image on the screen 104, which corresponds to an object, is formed at the distance L2 that is determined by the focal length of the concave mirror 105. Accordingly, when viewed from the occupant of the vehicle, the virtual image I is displayed at the distance of L1 and L2 from the front windshield 91. Assuming that the distance between the occupant of the vehicle and the front windshield 91 is L3, as illustrated in FIG. 3, the virtual image I is displayed (formed) at distance L (=L1+L2+L3) with reference to a viewpoint E of the occupant V of the vehicle.

At least some of the light flux to the front windshield 91 is reflected towards the viewpoint E of the occupant V of the vehicle. As a result, the occupant V of the vehicle can visually recognize the virtual image I, which is a magnified view of the intermediate image on the screen 104, through the front windshield 91. In other words, the virtual image I, which is a magnified view of the intermediate image, is displayed through the front windshield 91 when viewed from the occupant V of the vehicle.

Typically, the front windshield 91 is not flat but is slightly curved. For this reason, the image-forming position of the virtual image I is determined not only by the focal length of the concave mirror 105 but also by the curved surface of the front windshield 91, but the distance L is substantially determined by the distance L1+L2 as described above. When it is desired that the virtual image I be formed at a long distance so as to minimize the line-of-sight movement, the distance L1 or the distance L2 is lengthened. In order to lengthen the distance L1, the optical path may be turned by a mirror. In order to lengthen the distance L2, the focal length of the concave mirror 105 may be adjusted.

As the optical deformation in which the horizontal line of the intermediate image is distorted to be convex upward or downward is caused due to the effect of the front windshield 91, it is desired that at least one of the mirror 103 and the concave mirror 105 be designed and arranged so as to correct the optical deformation. Alternatively, it is desired that the projected image be corrected in view of the optical deformation.

A combiner may be arranged as a transmissive reflector on the viewpoint E side of the front windshield 91. In a configuration where a combiner is irradiated with the light reflected by the concave mirror 105, the virtual image I can be displayed in a similar manner to cases in which the front windshield 91 is irradiated with the light reflected by the concave mirror 105.

Figure 4:
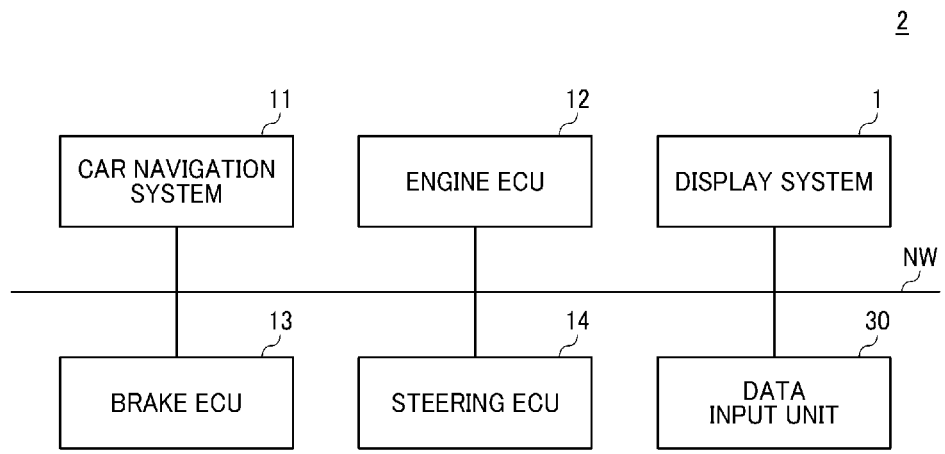
FIG. 4 is a block diagram illustrating a vehicle-installed system provided with a display system, according to an embodiment of the present disclosure.

A configuration in which the display system 1 is provided for a mobile object is described below with reference to FIG. 4. FIG. 4 is a block diagram illustrating a vehicle-installed system 2 in which the display system 1 is provided for a mobile object, according to the present embodiment. The vehicle-installed system 2 includes a car navigation system 11, an engine electronic control unit (ECU) 12, the display system 1, a brake ECU 13, a steering ECU 14, and the data input unit 30, each of which performs communication through an in-vehicle network (NW) such as a controller area network (CAN) bus.

The car navigation system 11 has a global navigation satellite system (GNSS) as typified by a global positioning system (GPS), and detects the current location of the vehicle and displays the position of the vehicle on the electronic chart. The car navigation system 11 accepts the input of the place of departure and the destination, and searches for the path from the place of departure to the destination. Moreover, the car navigation system 11 displays the position of the vehicle on the electronic chart, or guides the directions of travel to the occupant of the vehicle when the direction is to be changed soon, using, for example, voice, characters (that are displayed on a display), or animation. The car navigation system 11 may communicate with a server via, for example, the mobile phone network. In such a configuration, the server may send the electronic chart to the vehicle 9 or may search for the route.

The engine ECU 12 determines an optimal amount of fuel injection, advances or retards the ignition timing, or controls, for example, a valve mechanism, in view of the data obtained by various kinds of sensors and the status of the vehicle. For example, the engine ECU 12 refers to a map in which the shift lines for transmission are defined in response to the relation between the current vehicle speed and the degree of opening of the accelerator, and determines the necessity of speed change. The engine ECU 12 combines these kinds of controls to perform acceleration and deceleration control when the vehicle is tracking the preceding vehicle.

Even if the occupant of the vehicle does not press down on the brake pedal, the brake ECU 13 controls the braking and stopping power for each wheel of the vehicle. For example, control may be performed by an antilock braking system (ABS), or brake control may be performed when the vehicle is tracking the preceding vehicle. Moreover, automatic braking may be performed based on the time to collision (TTC) with an obstacle, or the stopped state may be maintained at hill start.

The steering ECU 14 detects the steering direction of the steering wheel and the amount of steering performed by the occupant of the vehicle, and performs power steering control to add steering torque in the steering direction. Even when the steering wheel is not operated by the occupant of the vehicle, the steering ECU 14 performs steering operation in a direction that prevents the vehicle from running off the traffic lane, in a direction that keeps the vehicle traveling forward in the center of the traffic lane, or in a direction that prevents the vehicle from approaching an obstacle.

The data input unit 30 is described below with reference to FIG. 5. The display system 1 can obtain the input information from the data input unit 30. The display system 1 may obtain information from an external network instead of the in-vehicle network NW.

A configuration of the data input unit 30 and the input data that is input by the data input unit 30 are described below with reference to FIG. 5.

Figure 5:
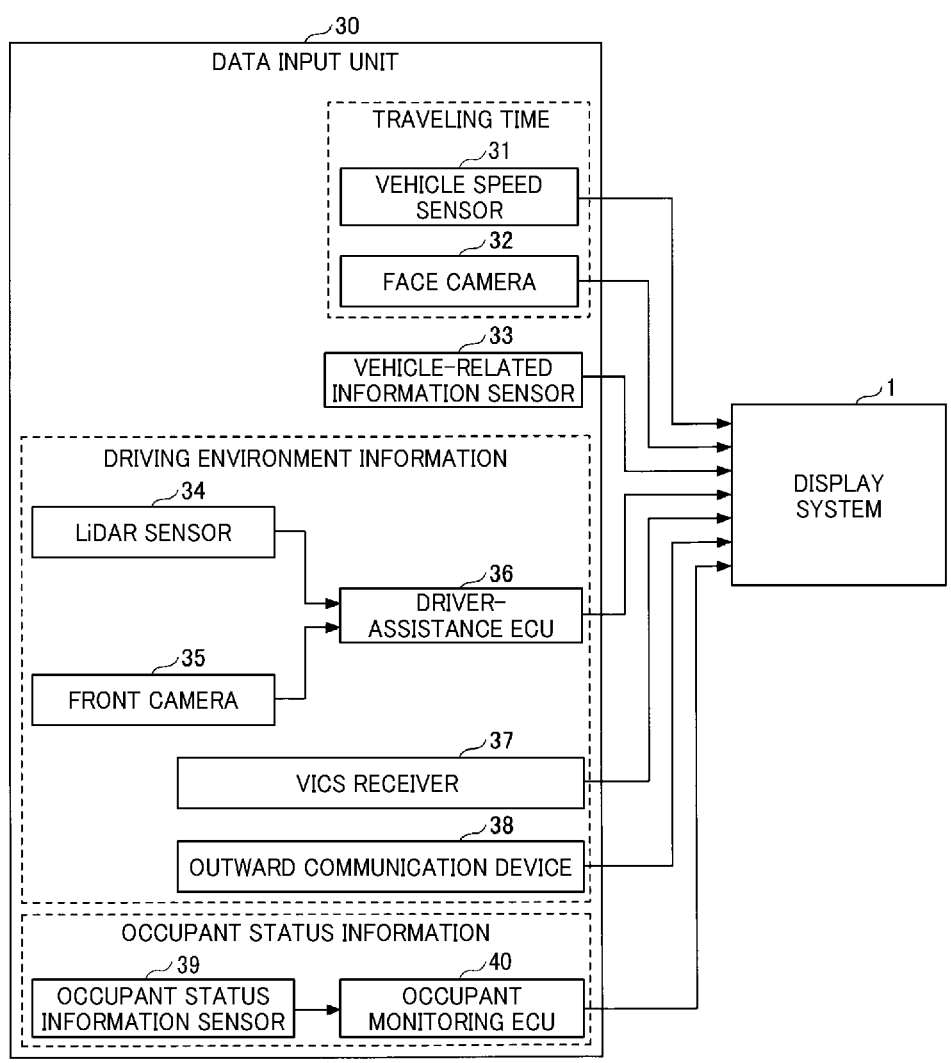
FIG. 5 is a diagram illustrating a configuration or structure of a data input unit of a vehicle-installed system, according to an embodiment of the present disclosure.

FIG. 5 is a diagram illustrating a configuration or structure of the data input unit 30 of the vehicle-installed system 2, according to the present embodiment.

The data input unit 30 obtains the above input data, and inputs the obtained input data to the display device 10. The data input unit 30 includes a face camera 32 and a vehicle speed sensor 31 used to obtain the traveling time, a vehicle-related information sensor 33 that obtains the vehicle-related information to be displayed by the display device 10, a light detection and ranging (LiDAR) sensor 34 and a front camera 35 that detect an object to obtain the driving environment information, a driver-assistance ECU 36 that assists the driving in relation to the object, a vehicle information communication system (VICS) receiver 37 and an outward communication device 38 that receive the driving environment information from an external device, an occupant status information sensor 39 that obtains the occupant status information, and an occupant monitoring ECU 40 that monitors the occupant based on the occupant status information. Whereas the traveling time, the driving environment information, and the occupant status information are used to determine the display mode of the display image to be displayed by the display device 10, the traveling time, the driving environment information, and the occupant status information may also be used as the display data to be displayed by the display device 10.

The vehicle speed sensor 31 has a sensor unit fixed to the car body, and the sensor unit detects a magnet that rotates together with a shaft of a drive train system. Moreover, a pulse wave proportionate to the rotation speed is generated, and the vehicle speed can be detected based on the number of the pulses per unit time. The face camera 32 captures the face of the occupant of the vehicle and performs face recognition to identify or visually recognize the occupant of the vehicle. Due to this configuration, the display system 1 can measure the traveling time for each occupant of the vehicle. Note also that the vehicle speed sensor 31 is a part of the vehicle-related information sensor 33.

The vehicle-related information sensor 33 includes an at least one sensor that detects the vehicle-related information other than the vehicle-related information detected by the vehicle speed sensor 31. For example, the vehicle-related information sensor 33 includes a fuel-gauge sensor, a shift-lever position sensor, an odometer, a tripmeter, a winker sensor (direction indicator sensor), and a water temperature sensor. However, no limitation is indicated thereby, and the vehicle-related information sensor 33 is satisfactory as long as it can obtain various kinds of vehicle-related information. The fuel-gauge sensor detects the current remaining fuel. The shift-lever position sensor detects the position of the shift lever manipulated by the occupant of the vehicle. The odometer accumulates the mileage of the vehicle to provide the total mileage. The tripmeter provides a sectional mileage between the point in time when the occupant of the vehicle initialized the tripmeter and the present time. The winker sensor (direction indicator sensor) detects the direction indicated by a winker (direction indicator) manipulated by the occupant of the vehicle. The water temperature sensor detects the temperature of engine cooling water. These items of information are merely an example of the information obtainable from the vehicle, and any other items of information obtainable from the vehicle can be the vehicle-related information. In the case of an electric-powered vehicle and a hybrid electric-internal combustion vehicle (hybrid car), for example, the remaining power in a battery, the amount of regenerative electric power, or the amount of power consumption may be obtained.

The LiDAR sensor 34 transmits radio signals around the vehicle. For example, in particular, the radio signals are transmitted ahead of the vehicle. Then, the LiDAR sensor 34 receives the returning radio signals as reflected by an object. A time-of-flight (TOF) method is known in the art where the distance to the object is measured based on the length of time between the instant when radio signals are transmitted and the instant when radio signals are reflected and received and the direction in which the object is placed is detected based on the direction in which the radio signals are transmitted. Alternatively, a method using the frequency modulation continuous wave (FMCW) are known in the art in which a mixed wave of a received wave and a transmitted wave is generated while continuously increasing the frequency of a transmitted wave and a beat frequency of a mixed wave that is caused by a slight difference in frequency is converted into distance. In such a method using the FMCW, the direction in which the object is placed is estimated by detecting a phase shift in received wave using a plurality of receiving antennas.

The front camera 35 is an imaging device that captures images ahead of the vehicle. The position at which the front camera 35 is attached is satisfactory as long as it can capture ahead of the camera. For example, the front camera 35 may be attached to the rear side of the rear-view mirror or near the rear-view mirror. The driver-assistance ECU 36 recognizes, for example, pedestrians, preceding vehicles, road signs, and painting on the road such as a white line, based on the image data captured by the front camera 35. The front camera 35 may be either a monocular camera or a stereo camera. In the case of a monocular camera or a stereo camera that can obtain distance information, the LiDAR sensor 34 is not always necessary. However, when the LiDAR sensor 34 is used in addition to the front camera 35 that can obtain distance information, fusion between the distance information obtained by the front camera 35 and the distance information obtained by the LiDAR sensor 34 can be performed, and distance information of high degree of precision in which the disadvantages of a pair of items of distance information are complemented each other can be obtained. In addition to the LiDAR sensor 34 and the front camera 35, for example, a sonic sensor (ultrasonic sensor) may be provided. Alternatively, a rear camera or a side camera may be provided in addition to the front camera 35.

The driver-assistance ECU 36 performs various kinds of driver assistance based on the distance information of the object detected by at least one of the LiDAR sensor 34 and the front camera 35, in cooperation with the engine ECU 12, the brake ECU 13 and the steering ECU 14. For example, acceleration and deceleration control when the vehicle is tracking the preceding vehicle, automatic braking, prevention of the vehicle from running off the traffic lane, lane-keeping, and steering to avoid an obstacle as described above are performed. In the acceleration and deceleration control, the driver-assistance ECU 36 controls the motive power and the braking and stopping power so as to maintain the desired distance that varies depending on the vehicle speed. In the automatic braking, for example, an alert image or sound that calls attention to the occupant of the vehicle, an image that prompts the driver to press down on the brake pedal, and rolling up of the seatbelt and anti-collision braking when there is a high probability of collision are performed depending on the time to collision (TTC). In the prevention of the vehicle from running off the traffic lane, the driver-assistance ECU 36 recognizes the white lines (lines that divide traffic lanes) from the captured image data, and adds steering torque to the direction opposite to the direction of running off the traffic lane.

In lane keeping, the center of the traffic lane is set as the target driving line, and steering torque proportional to the deviation from the target driving line is added to the direction opposite to the deviation.

In the steering to avoid an obstacle, when it is determined that the collision cannot be avoided by braking, a driving line for avoiding the obstacle is determined, and steering torque for traveling along the determined driving line is added is added.

Moreover, the driver-assistance ECU 36 detects that the preceding vehicle is driving off, and instructs the display system 1 to sound an alarm or display an image to encourage the occupant of the vehicle to start driving. Further, the driver-assistance ECU 36 detects that the steering wheel is not operated for a long time, and instructs the display system 1 to sound an alarm or display an image to encourage the occupant of the vehicle to hold the steering wheel.

In accordance with such controls as above, the driver-assistance ECU 36 instructs the display system 1 to output, for example, at least one of various kinds of image (icon) and characters (texts). Some example displays are described below with reference to FIG. 8A, FIG. 8B, FIG. 8C, FIG. 8D, FIG. 8E, and FIG. 8F. Alternatively, the driver-assistance ECU 36 may instruct the display system 1 to sound an alarm.

The VICS receiver 37 receives a radio or radar signal distributed by the VICS. Note that the vehicle information communication system (VICS) is a system that transmits the traffic information such as traffic congestion and traffic restrictions to a vehicle-installed device in real time using frequency modulation (FM) multiplex broadcasting or a beacon. The outward communication device 38 is connected to the Internet or the like via the network such as of 3G, 4G, 5G, LTE, and wireless LAN, and receives various kinds of information. For example, the outward communication device 38 can receive weather information such as of rain, snow, and fog. Alternatively, the outward communication device 38 may receive, for example, news, music, and video data. Moreover, the outward communication device 38 can obtain, for example, the status information of a traffic signal and the time it takes before the signal changes. As described above, the VICS receiver 37 and the outward communication device 38 may perform road/automobile communication. Further, the outward communication device 38 may obtain the information detected by another vehicle through car-to-car communication.

The occupant status information sensor 39 is a sensor that obtains the occupant status information that is directly or indirectly detected from the occupant of the vehicle. The occupant status information sensor 39 is, for example, an electrocardiogram sensor, a heart rate sensor, a blood pressure sensor, a body temperature sensor, a pulse sensor, a respiration sensor, a perspiration sensor, a blinking sensor, a pupil sensor, a brain wave sensor, or a myoelectric potential sensor. For example, a wristwatch-type wearable device (smart watch) that is worn by the occupant of the vehicle may serve as the occupant status information sensor 39. An electrode is disposed on the rear of the wearable device and at a part of the wearable device other than the rear of the wearable device, respectively, and such electrodes detect electric current when a user touches for certain length of time the electrode that is disposed at a part of the wearable device other than the rear of the wearable device. As the electric current reflects the myocardial activity, electrocardiogram information can be obtained by analyzing the electric current. The heart rate can be derived from the electrocardiogram information, and the breathing rate is obtained in view of the fact that the impedance (electrical resistance) between a pair of electrodes changes according to the respiration. A light-emitting diode (LED) light source and a photodiode (PD) may be provided for the wearable device, and the photodiode receives the light reflected from the blood vessels that are irradiated by the LED. As the density of erythrocytes (red blood cells) changes according to the pulsation of the heart rate, the heart rate information and the pulse information are obtained by analyzing the changes in the density of erythrocytes. The blood pressure information can be obtained from the heart rate and the flow of blood. The body temperature information can be detected by a temperature sensor, and the perspiration information is detected as, for example, the degree of moisture content or humidity. The myoelectric potential is a change in electrical potential on the surfaces of skin caused by the movement of muscles, and is obtained by analyzing the signals of an electrode pasted on a specific area of the muscles. The blinking information and pupil information are obtained by analyzing the facial images that are captured by the face camera 32. The drowsiness can be estimated by monitoring the eyes of the face and how much the eyes are open. Moreover, the drowsiness (arousal level) can be estimated by detecting the black points of the eyes in the center as pupils. Further, the brain waves can be detected in a non-invasive manner using a sensor of head band type or helmet type in which a plurality of electrodes are inwardly arranged.

The occupant status information sensor 39 may communicate with the display system 1 through a wireless connection such as Bluetooth (registered trademark), or may communicate through a wired connection such as a universal serial bus (USB) cable. Some concrete examples of the occupant status information and the occupant status information sensor 39 are described as above, but no limitation is intended thereby. Some examples of how the occupant status information is analyzed are described as above, but no limitation is indicated thereby, and any method of analyzing the occupant status information may be used.

The occupant monitoring ECU 40 outputs the results of monitoring the occupant of the vehicle to the display system 1 based on the occupant status information. For example, the occupant monitoring ECU 40 instructs the display system 1 to output at least one of a message or image saying "Stop driving right now" or "Take a break" when a sign of ventricular fibrillation is observed from the electrocardiogram information, when the heart rate, pulse, or the breathing rate is equal to or higher than a threshold, when the blood pressure is equal to or higher than a threshold or when the blood pressure is lower than a threshold, when the body temperature is equal to or higher than a threshold, when the amount of perspiration is equal to or larger than a threshold, when it is determined that the arousal level is low, when some abnormalities are observed in the brain wave, or when it is determined that some muscles are tired. Alternatively, the occupant status information may be displayed in a direct manner, or the occupant monitoring ECU 40 may instruct the display system 1 to sound an alarm.

A hardware configuration of the display controller 20 according to the present embodiment is described below with reference to FIG. 6.

Figure 6:
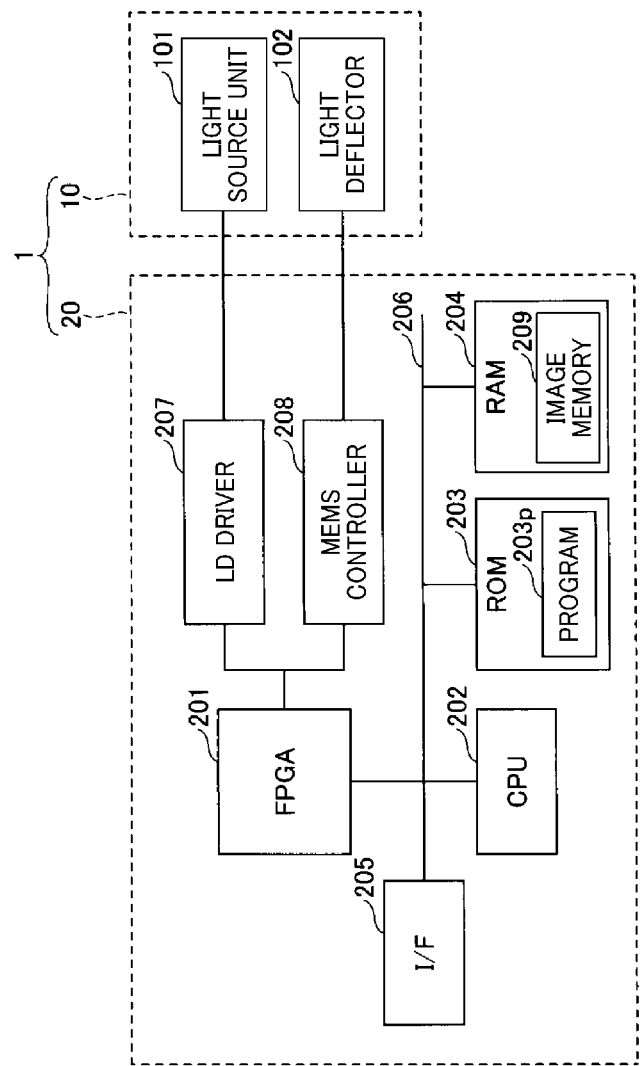
FIG. 6 is a diagram illustrating a hardware configuration of a display controller according to an embodiment of the present disclosure.

FIG. 6 is a diagram illustrating a hardware configuration of the display controller 20 according to the present embodiment.

The display controller 20 includes a field-programmable gate array (FPGA) 201, a central processing unit (CPU) 202, a read only memory (ROM) 203, a random access memory (RAM) 204, an interface (I/F) 205, a bus line 206, a laser diode (LD) driver 207, and a micro-electromechanical systems (MEMS) controller 208. The FPGA 201, the CPU 202, the ROM 203, the RAM 204, and the interface 205 are interconnected through the bus line 206.

The CPU 202 controls the multiple functions of the display controller 20. The ROM 203 stores a program 203$p$ that is executed by the CPU 202 to control the multiple functions of the display controller 20. The RAM 204 is used as a work area in which the program 203$p$ is developed and the CPU 202 executes the program 203$p$. The RAM 204 includes an image memory 209. The image memory 209 is used to generate an image to be projected as a virtual image I. The interface 205 is an interface used to communicate with the data input unit 30, and is connected to, for example, a controller area network (CAN) bus of the vehicle 9 or the Ethernet (registered trademark).

The FPGA 201 controls the LD driver 207 based on the image generated by the CPU 202. The LD driver 207 drives the laser diodes (LDs) of the light source unit 101 of the display device 10 to control the light emission of the LDs based on the image. The FPGA 201 drives the light deflector 102 of the display device 10 through the MEMS controller 208 such that the laser beams will be deflected in a direction corresponding to the position of each pixel of the image.

A functional configuration of the display controller 20 according to the present embodiment is described below with reference to FIG. 7.

Figure 7:
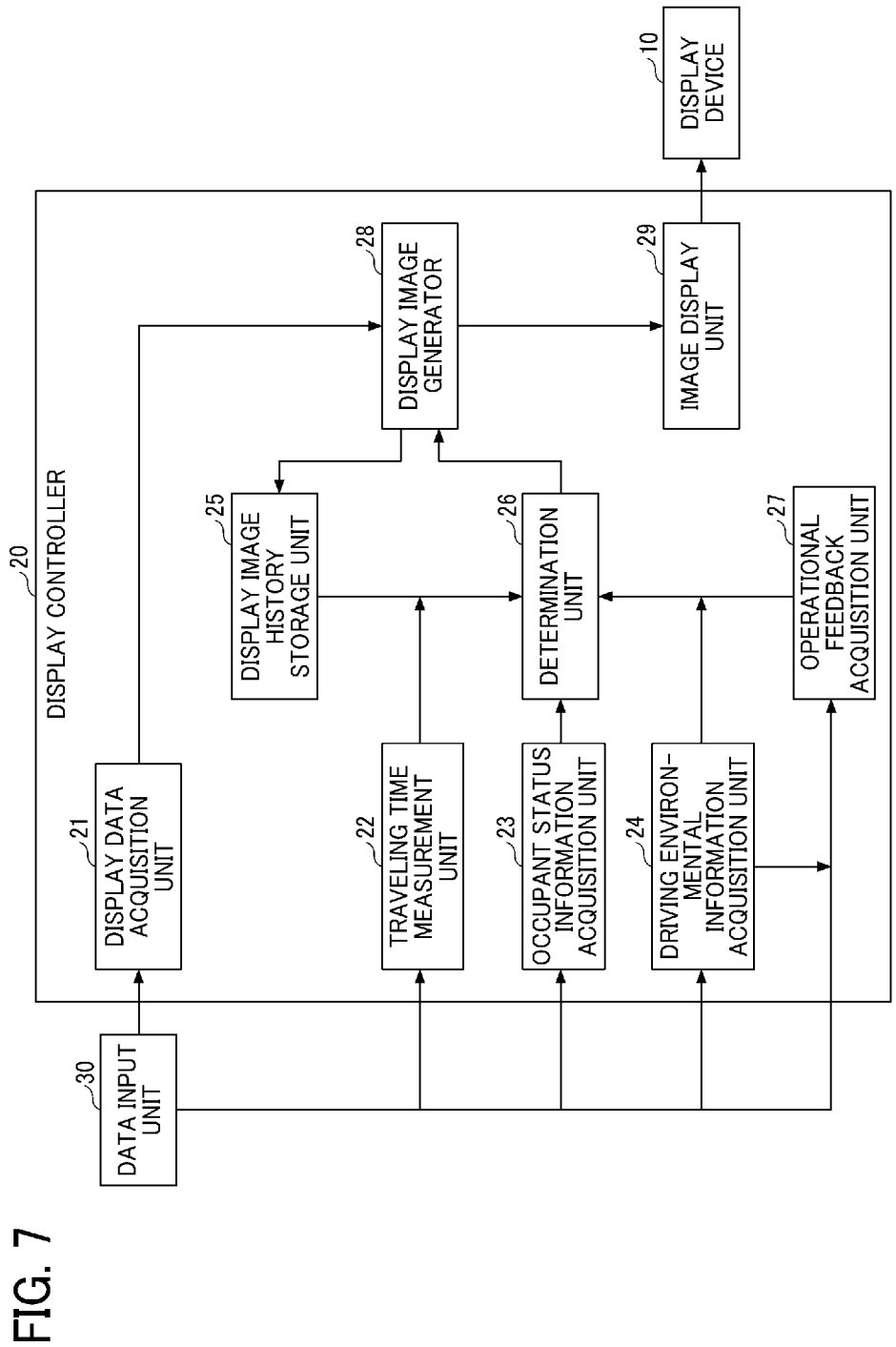
FIG. 7 is a functional block diagram of a display controller according to an embodiment of the present disclosure.

FIG. 7 is a functional block diagram of the display controller 20 according to the present embodiment.

The display controller 20 includes a display data acquisition unit 21, a traveling time measurement unit 22, an occupant status information acquisition unit 23, a driving environmental information acquisition unit 24, a display image history storage unit 25, a determination unit 26, an operational feedback acquisition unit 27, a display image generator 28, and an image display unit 29. These functions of the display controller 20 are implemented as the CPU 202 executes the program 203$p$ developed from the ROM 203 to the RAM 204 of the display controller 20.

The display data acquisition unit 21 obtains the display data to be displayed by the display device 10 from the input data that is input from the data input unit 30. For this reason, the display data may be equivalent to the input data or a part of the input data. For example, the display data may be the vehicle speed, at least one item of vehicle-related information, the driving environment information, or the occupant status information or a message derived from the occupant status information. However, it is not necessary to display all the items of display data.

The traveling time measurement unit 22 obtains the vehicle speed obtained by the vehicle speed sensor 31, and accumulates the length of time during which the vehicle speed is equal to or faster than zero. As a result, the traveling time since the vehicle started driving can be measured. For example, it is assumed that the vehicle starts driving at the timing when the ignition is turned on (or the timing at which the system is turned on for vehicles whose motive power is generated by electric motors). In the following description, the timing when the ignition is turned on may be referred to as "IG-ON." Instead of initializing the traveling time every time the ignition is turned on (IG-ON), the traveling time may be accumulated on a daily basis. For example, the traveling time measurement unit 22 may measure the traveling time for every owner of the vehicle that is identified by the face camera 32. When the traveling time is accumulated, the traveling time may be weighted according to the weather or the like.

The driving environmental information acquisition unit 24 obtains the driving environment information. The obtained driving environment information may be sent to the determination unit 26 as it is, or may be sent to the determination unit 26 upon performing some sort of processing on the obtained driving environment information. As an example of such processing, the driving environment information may be classified into several groups, and the group ID that is obtained as a result of classification may be sent to the determination unit 26.

First Group: Driving environment information that does not affect the attentional resources that are related to the driving operation to be performed by the owner of the vehicle Second Group: Driving environment information that reduces the attentional resources that are related to the driving operation to be performed by the owner of the vehicle Third Group: Driving environment information that is estimated to require a greater amount of attentional resources for the driving operation to be performed by the owner of the vehicle The driving environment information that belongs to the first group is the driving environment information for which the owner of the vehicle does not have to perform any particular driving operation. For example, the driving environment information that belongs to the first group includes a mark indicating that the vehicle is tracking the preceding vehicle and an icon of the traffic lane that indicates information expressed by figures or patterns. The driving environment information that belongs to the second group is the driving environment information for which the owner of the vehicle has to perform some sort of driving operation. Note that the degree of urgency of the driving environment information that belongs to the second group is relatively lower than that of the driving environment information that belongs to the third group. The driving environment information that belongs to the second group includes, for example, an indication that prompts the occupant of the vehicle to hold the steering wheel and a warning that provides notification that the preceding vehicle is driving off. The driving environment information that belongs to the third group is the driving environment information for which the owner of the vehicle has to perform some sort of driving operation. Note that the degree of urgency of the driving environment information that belongs to the third group is relatively higher than that of the driving environment information that belongs to the second group. The driving environment information that belongs to the third group includes, for example, an indication that prompts the driver to press down on the brake pedal, a warning indicating that the vehicle may be running off the traffic lane, and a warning indicating that anti-collision braking has been performed.

The driving environmental information acquisition unit 24 accumulates the number of times each one of the driving environment information that belongs to the first, second, and the third group is displayed, and sends the obtained number of times each one of the driving environment information that belongs to the first, second, and the third group is displayed to the determination unit 26. The driving environmental information acquisition unit 24 provides notification of a recommendable operation to be performed by the occupant of the vehicle (such as starting the vehicle, holding the steering wheel, steering, and pressing down the brake pedal), which is a part of the driving environment information that belongs to the second and third groups, to the operational feedback acquisition unit 27.

The operational feedback acquisition unit 27 obtains the information about the operation performed by the occupant of the vehicle from the data input unit 30. For example, the operational feedback acquisition unit 27 obtains the information about the vehicle speed, pressing down on the brake pedal, holding the steering wheel, steering the steering wheel. The operational feedback acquisition unit 27 measures the delay time between the timing at which the recommendable operation is obtained and the timing at which the information about the operation specified by the recommendable operation is input, and determines the state of the attentional resources of the occupant of the vehicle based on the obtained delay time. In other words, a long delay time indicates that it takes a long time for the occupant of the vehicle to actually perform the driving operation after a display image is visually recognized. Accordingly, when the delay time is long, it can be estimated that the attentional resources for visually recognizing a display image or the attentional resources for driving operation are decreased. In view of the above circumstances, the operational feedback acquisition unit 27 sends the delay time to the determination unit 26.

The occupant status information acquisition unit 23 obtains the above occupant status information. The occupant status information acquisition unit 23 may convert the occupant status information into the amount of reduction in attentional-resources consumption. As the occupant status information is influenced by the physical and mental state or the health, it is considered that the occupant status information correlates with the remaining amount of attentional resources. For example, when the heart rate is high, it is estimated that the occupant of the vehicle is under tension and the attentional resources of the occupant of the vehicle are low. The occupant status information acquisition unit 23 uses, for example, a function in the equation given below to convert the occupant status information into the amount of reduction in attentional-resources consumption.

Amount of Reduction in Attentional—resources Consumption=a×Existence or Nonexistence of Ventricular Fibrillation+b×Heart Rate+c×Blood Pressure+d×Body Temperature+f×Pulse Rate+g×Respiration Rate+h×Amount of Perspiration+i×Arousal Level+j×Characteristics of Brain Wave+k×Myoelectric Potential The display image generator 28 generates the display image to be displayed by the display device 10 based on the display data obtained by the display data acquisition unit 21. For example, when the vehicle speed or vehicle-related information is to be displayed, generates, for example, a predetermined icon in addition to a numerical value and a character. When the driving environment information is to be displayed, for example, a mark indicating that the vehicle is tracking the preceding vehicle, an icon of the traffic lane, a character or icon indicating that the vehicle may be running off the traffic lane, a character or icon that calls attention to the occupant of the vehicle, a character or icon that prompts the occupant of the vehicle to press down the brake pedal, a character or icon indicating that anti-collision braking has been performed, a character or icon that prompts the occupant of the vehicle to hold the steering wheel, a character or icon that provides notification that the preceding vehicle is driving off is generated based on the distance information detected by various kinds of sensors such as a light detection and ranging (LiDAR) device and a camera. When the occupant status information is to be displayed, for example, a message saying "Stop driving right now" or "Take a break" is generated.

The image display unit 29 controls the LD driver 207 and the MEMS controller 208 to instruct the display device 10 to display a display image.

The display image history storage unit 25 stores the history of the display image generated by the display image generator 28. More specifically, the display image generator 28 generates, for example, a numerical value, a character, or an icon according to the input data, and instructs the image display unit 29 to display the generated data. Then, the display image history storage unit 25 stores the history of the displayed display images. As characteristics of human, the amount of attentional resources decreases as he or she visually recognizes a larger number of images. This is because not only the degree of fatigue but also habituation to the same stimulus or the like affects the attentional resources. The display image history storage unit 25 converts the display image history into the amount of attentional-resources consumption, and sends the obtained the amount of attentional-resources consumption to the determination unit 26, as will be described later in detail.

The determination unit 26 determines whether or not there is a necessity to change the display mode of the display image based on at least one of the traveling time, driving environment information, occupant status information, and the display image history. In other words, the determination unit 26 determines whether or not the total amount of attentional resources has decreased. For example, the determination unit 26 determines whether the amount of attentional resources that is to be allocated to the visual recognition of information has decreased. In other words, the determination unit 26 determines whether the display image is to be displayed in a display mode where information can visually be recognized with a smaller amount of attentional resources. The determination unit 26 sends the result of the determination and the degree of change indicating how and how much the display mode is to be changed to the display image generator 28.

Due to such configurations as described above, the display controller 20 determines the display mode of the display image to be displayed by the display device 10 based on the degree of change. In other words, the information is displayed in a display mode where information can visually be recognized with a smaller amount of attentional resources. In addition to a method in which the size or thickness of text or character is changed as described above with reference to FIG. 1, for example, the brightness may be enhanced, or the color of the background of the image of contents of data may be changed to the complementary color of the color of the image of contents of data. Moreover, the level of color saturation may be increased, or the distance to a virtual image may be increased, or the image of the contents of data may be flashed.

The conversion of the display image history into the amount of attentional-resources consumption, which is performed by the display image history storage unit 25, is described with reference to tables A and B given below.

TABLE A (a)

| DISPLAY-IMAGE ID | DISPLAY COUNT |
| --- | --- |
| 001 | 3 |
| 002 | 2 |
| 003 | 5 |
| 004 | 11 |
| ... | |

TABLE B (b)

| DISPLAY-IMAGE ID | COLOR | BRIGHT-NESS | SIZE | POSITION | TYPE (1. CHARACTER 2. ICON) |
| --- | --- | --- | --- | --- | --- |
| 001 | 2 | 2 | 5 | 3 | 1 |
| 002 | 5 | 2 | 4 | 3 | 2 |
| 003 | 3 | 3 | 3 | 3 | 1 |
| 004 | 4 | 2 | 2 | 3 | 2 |
| ... | | | | | |

Table A is an example of the display image history stored by the display image history storage unit 25.

In the display image history, each display count is recorded in association with the display-image ID. The display-image ID is the identification information used to uniquely identify or measure the display image that is generated by the display image generator 28. The display image history storage unit 25 can use the display-image ID to specify which of, for example, the vehicle speed and the tracking mark is displayed. The term "display count" indicates the number of times each one of the display images is displayed. Regarding the information that is displayed on a continual basis such as the vehicle speed, the number of times the information is displayed (display count) is counted at regular time intervals. Alternatively, the display time may be measured. In a similar manner to the traveling time, the counting of display count starts when the vehicle starts driving for every owner of the vehicle.

The display image history storage unit 25 has a conversion table depicted as above as Table B, and this conversion table is used to convert the display image history into the amount of attentional-resources consumption. In the conversion table, the scores of the color, brightness, size, position, and the type of display image are determined in association with the display image ID. The color, brightness, size, position, and the type of display image are parameters of the display image that affect the amount of attentional-resources consumption, and those parameters are determined for each display image in advance. Regarding the color of the display image, the amount of attentional-resources consumption is small when the display image is in red color that attracts more attention than other colors. Regarding the brightness of the display image, the amount of attentional-resources consumption decreases as the levels of brightness is higher. Regarding the brightness of the display image, the amount of attentional-resources consumption decreases as the levels of brightness is higher. Regarding the size of the display image, the amount of attentional-resources consumption decreases as the size is larger. Regarding the position of the display image, the amount of attentional-resources consumption decreases as the position gets closer to the line-of-vision direction or the center of the display image. Regarding the type of display image, the amount of attentional-resources consumption is small when the display image is an icon.

The display image history storage unit 25 uses, for example, the following equation to convert the display image history into the amount of attentional-resources consumption.

Amount of Attentional-resources Consumption=Display Count×(Color+Brightness+Size+Position+Type)

Due to the configurations as described above, the display image history can be converted into the amount of attentional-resources consumption. The above conversion formula is given by way of example, and no limitation is indicated thereby.

Some example display images according to the present embodiment are described below with reference to FIG. 8A, FIG. 8B, FIG. 8C, FIG. 8D, FIG. 8E, and FIG. 8F.

FIG. 8A, FIG. 8B, FIG. 8C, FIG. 8D, FIG. 8E, and FIG. 8F are diagrams each illustrating a different display image displayed by the display device 10, according to the present embodiment.

Figure 8A:
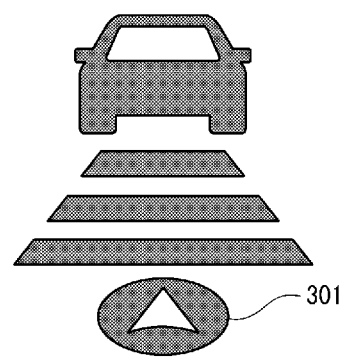
FIG. 8A, FIG. 8B, FIG. 8C, FIG. 8D, FIG. 8E, and FIG. 8F are diagrams each illustrating a different display image displayed by a display device, according to an embodiment of the present disclosure.

Firstly, FIG. 8A is an image including a mark 301 that indicates that the vehicle is tracking a preceding vehicle, as an example display image indicative of the status of various kinds of controls based on the information detected by various kinds of sensors such as a light detection and ranging (LiDAR) device and a camera, according to the present embodiment. The mark 301 that points at the preceding vehicle indicates the controlling processes to track the preceding vehicle are in operation.

Figure 8B:
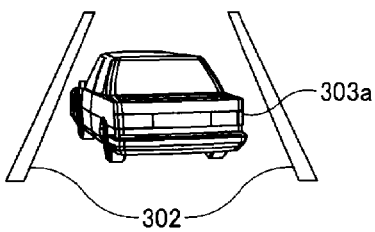

FIG. 8B is an image including a pair of icons 302 indicative of the traffic lane and a character or icon indicating that the vehicle may be running off the traffic lane, according to the present embodiment.

In order to show concern that the vehicle may be running off the traffic lane is indicated, an icon 303a indicative of the vehicle is inclined with reference to the pair of icons 302 indicative of the traffic lane and a message 303b saying "Watch the line" is displayed.

Figure 8C:
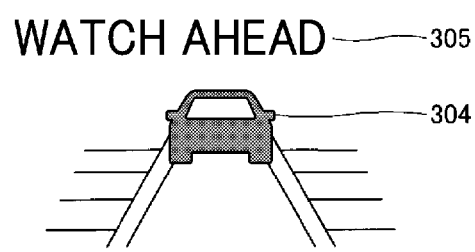

FIG. 8C is an image including a character and some icons that call attention to the occupant of the vehicle based on the time to collision (TTC) with an object, according to the present embodiment.

More specifically, the image of FIG. 8C indicates that attention should be paid to the distance to the object by an icon 304 of a preceding vehicle and a message 305 saying "watch ahead."

Figure 8D:
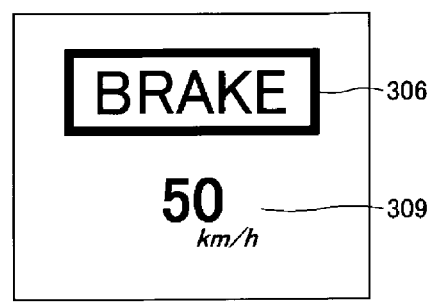

FIG. 8D is an image including a character or icon that prompts the occupant of the vehicle to press down the brake pedal, according to the present embodiment.

More specifically, a message 306 saying "BRAKE" indicates that the brake pedal should be pressed down.

Figure 8E:
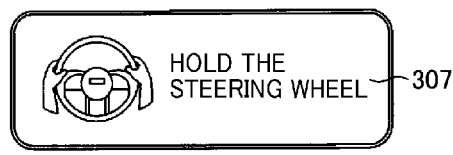

FIG. 8E is an image including texts (characters) and an icon that prompt the occupant of the vehicle to hold the steering wheel, according to the present embodiment.

More specifically, a message 307 saying "Hold the steering wheel" prompts the occupant of the vehicle to hold the steering wheel.

Figure 8F:
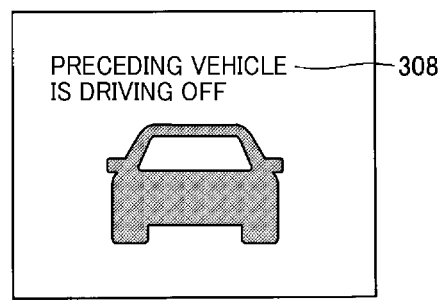

FIG. 8F is an image including texts (characters) and an icon that provides notification that the preceding vehicle is driving off, according to the present embodiment.

More specifically, a message 308 saying "Preceding vehicle is driving off" indicates that the preceding vehicle is driving off.

The display image generator 28 changes the way of presenting these display images (i.e., the display mode of these display images) based on the result of the determination and the degree of change sent from the determination unit 26. Note also that any one of the display images may flash or move like animation. For example, a moving pedestrian or the approaching direction of another vehicle may be indicated by animation, or the white lines may be flashed or blinked. Alternatively, in some cases, an alarm may ring where appropriate. Note also that any of the display images may be a still image or moving images.

Some ways of changing the display mode to a display mode where information can visually be recognized with a smaller amount of attentional resources are described below with reference to FIG. 9A-1, FIG. 9A-2, FIG. 9B-1, FIG. 9B-2, FIG. 9C-1, FIG. 9C-2, FIG. 10A-1, FIG. 10A-2, FIG. 10B-1, FIG. 10B-2, FIG. 10C-1, and FIG. 10C-2.

FIG. 9A-1, FIG. 9A-2, FIG. 9B-1, FIG. 9B-2, FIG. 9C-1, and FIG. 9C-2 are diagrams each illustrating a display mode where the size or thickness of text or character and the brightness are changed and complementary colors are used, according to the present embodiment.

Figures 1, 9A:
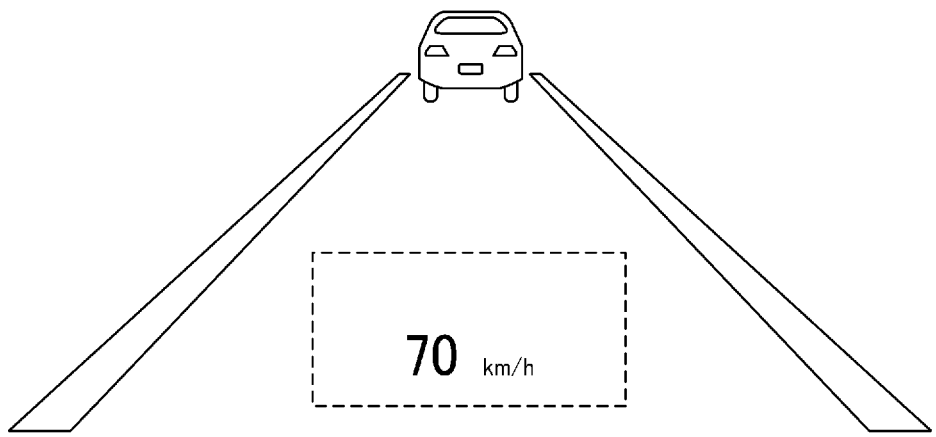
Figures 2, 9A:
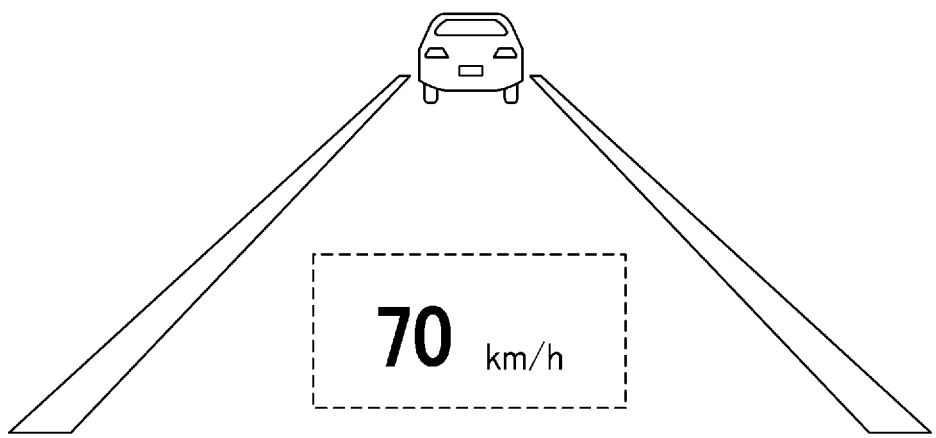

FIG. 9A-1 is a diagram illustrating the way of presenting some display images (i.e., the display mode of some display images) whose size and thickness are not-yet changed, according to the present embodiment.

FIG. 9A-2 is a diagram illustrating the way of presenting a display image (i.e., the display mode of a display image) whose display position is changed, according to the present embodiment.

In FIG. 9A-2, the size and thickness of the texts (characters) are increased. Accordingly, the occupant of the vehicle can visually recognize the texts (characters) with a smaller amount of attentional resources.

Figures 1, 9B:
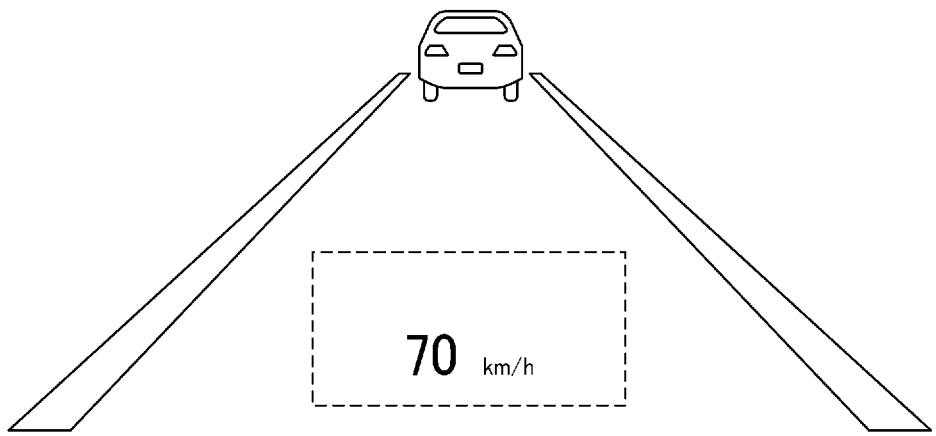
Figures 2, 9B:
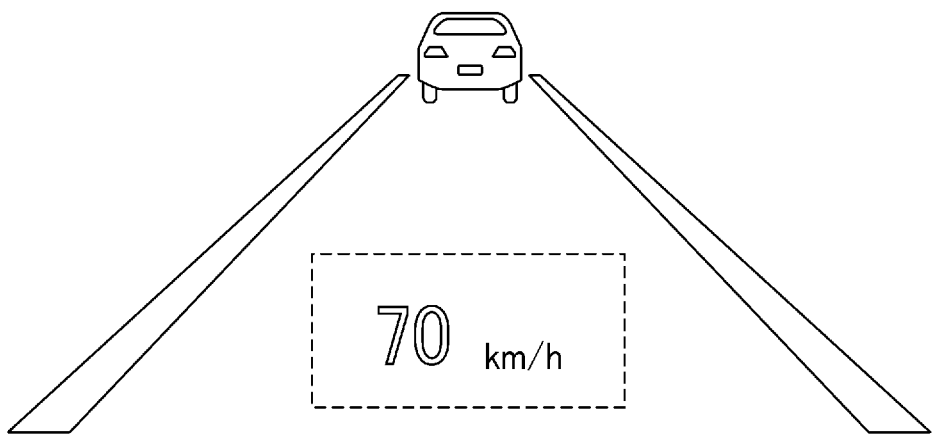

FIG. 9B-1 is a diagram illustrating the way of presenting a display image (i.e., the display mode of a display image) whose brightness is not-yet changed, according to the present embodiment.

FIG. 9A-2 is a diagram illustrating the way of presenting a display image (i.e., the display mode of a display image) whose display position is changed, according to the present embodiment.

In FIG. 9B-2, the brightness of a display image is increased. Accordingly, the occupant of the vehicle can visually recognize the display image with a smaller amount of attentional resources.

Figures 1, 9C:
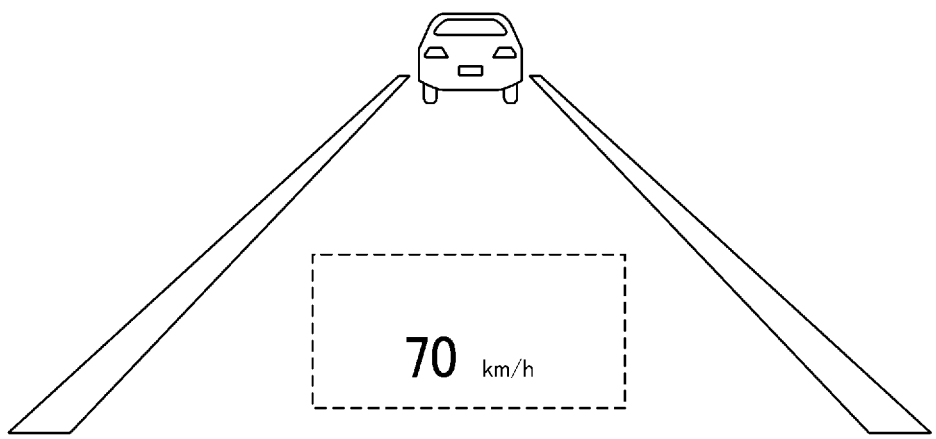
Figures 2, 9C:
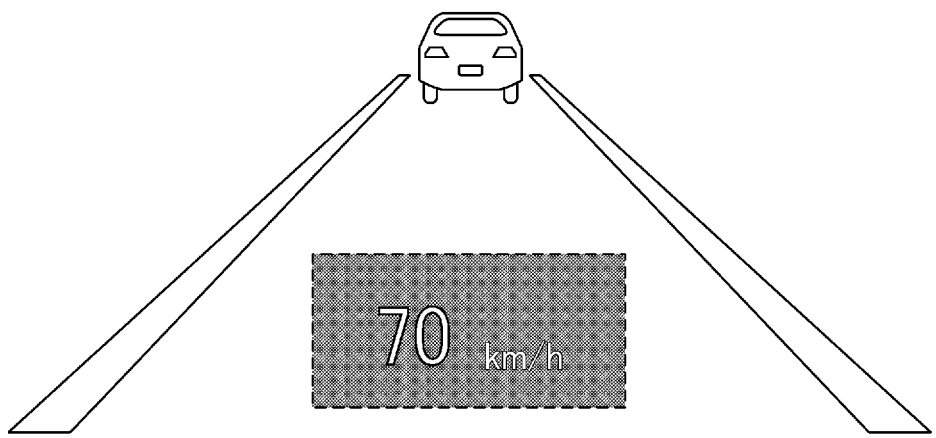

FIG. 9C-1 is a diagram illustrating the way of presenting a display image (i.e., the display mode of a display image) where some colors are not-yet changed to a pair of complementary colors, according to the present embodiment.

FIG. 9C-2 is a diagram illustrating the way of presenting a display image (i.e., the display mode of a display image) whose display position is changed, according to the present embodiment.

In FIG. 9C-2, the color of the background image is complementary to the color of the particular contents of data of the display image (i.e., the vehicle speed in this example). Accordingly, the occupant of the vehicle can visually recognize the display image with a smaller amount of attentional resources. When a certain color is complementary to a different color, those colors are positioned diametrically opposite to each other in the color wheel, and one of such a pair of colors can make the other color stand out. For example, yellow is complementary to purple.

FIG. 10A-1, FIG. 10A-2, FIG. 10B-1, FIG. 10B-2, FIG. 10C-1, and FIG. 10C-2 are diagrams each illustrating a change in display mode where the level of color saturation or the distance to a virtual image is changed, or flashing is used, according to the present embodiment.

Figures 1, 10A:
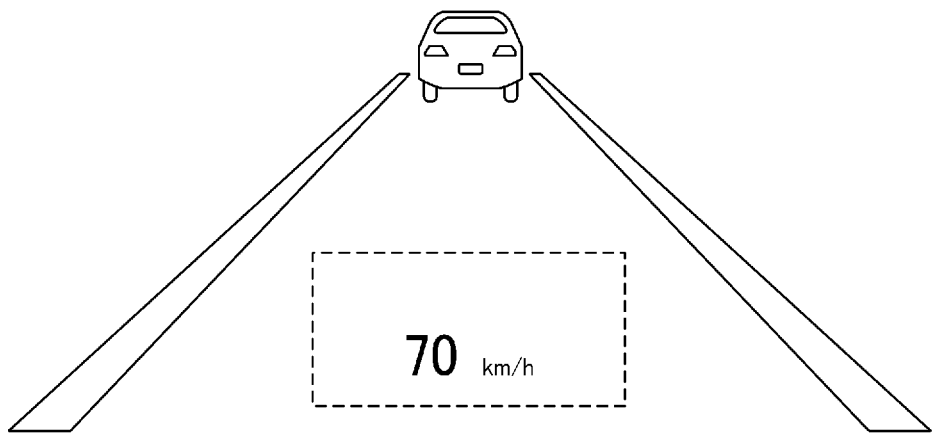
Figures 2, 10A:
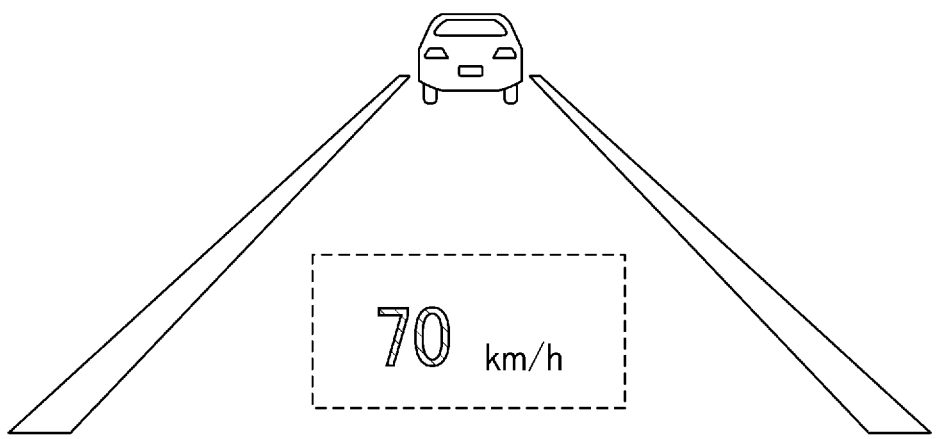

FIG. 10A-1 is a diagram illustrating the way of presenting a display image (i.e., the display mode of a display image) whose saturation is not-yet changed, according to the present embodiment.

FIG. 10A-2 is a diagram illustrating the way of presenting a display image (i.e., the display mode of a display image) whose display position is changed, according to the present embodiment.

In FIG. 10A-2, the level of color saturation of characters (texts) is increased. Accordingly, the occupant of the vehicle can visually recognize the characters (texts) with a smaller amount of attentional resources.

Figures 1, 10B:
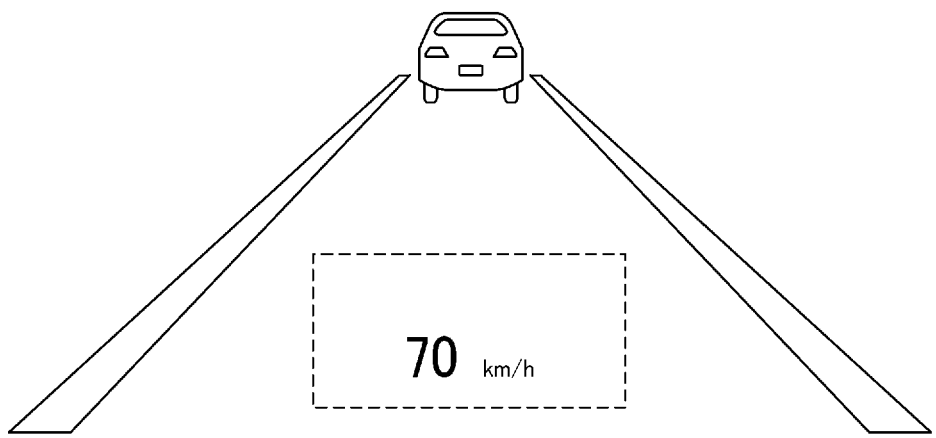
Figures 2, 10B:
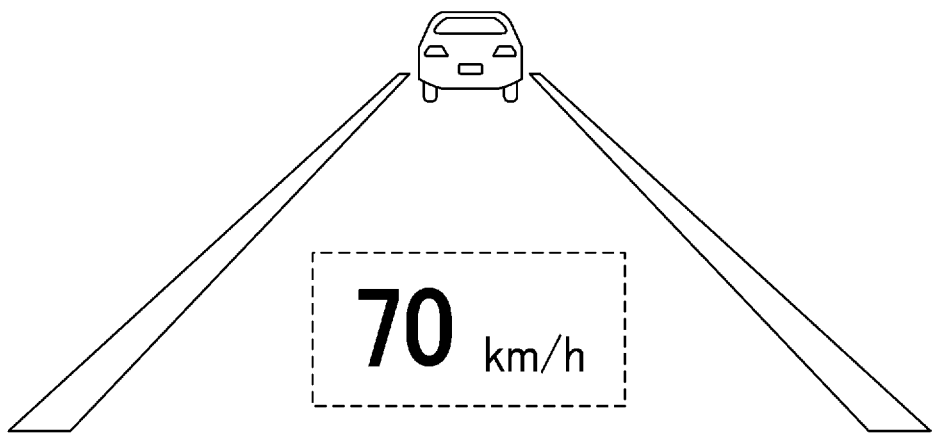

FIG. 10B-1 is a diagram illustrating the way of presenting a display image (i.e., the display mode of a display image) whose distance to the virtual image is not-yet changed, according to the present embodiment.

FIG. 10B-2 is a diagram illustrating the way of presenting a display image (i.e., the display mode of a display image) whose display position is changed, according to the present embodiment.

In FIG. 10B-2, the distance to the virtual image is lengthened, and thus the virtual image appears larger when viewed by the occupant of the vehicle. Accordingly, the occupant of the vehicle can visually recognize the virtual image with a smaller amount of attentional resources. In order to increase the distance to the virtual image, the optical-path length from the concave mirror 105 to the front windshield 91 may be increased. For example, the light may be turned several times as reflected by a plurality of mirrors.

Figures 1, 10C:
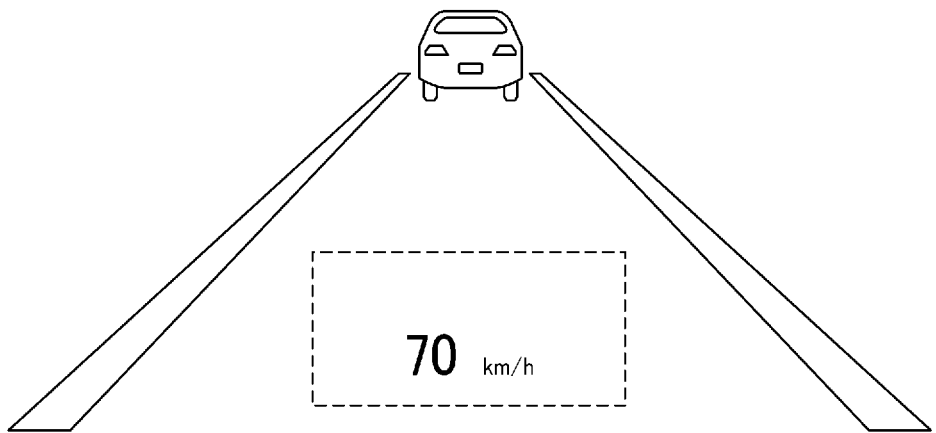
Figures 2, 10C:
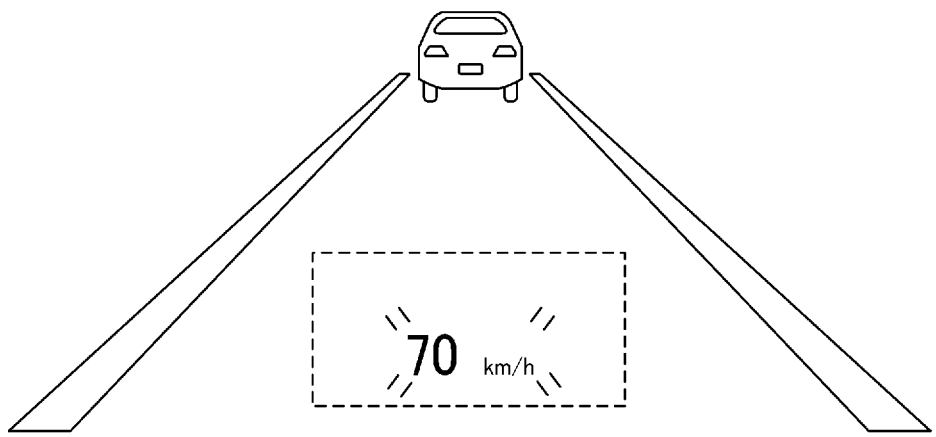

FIG. 10C-1 is a diagram illustrating the way of presenting a display image (i.e., the display mode of a display image) that is not-yet flashing, according to the present embodiment.

FIG. 10C-2 is a diagram illustrating the way of presenting a display image (i.e., the display mode of a display image) that is flashing, according to the present embodiment.

As the display image flashes in FIG. 10C-2, the display image stands out. Accordingly, the occupant of the vehicle can visually recognize the display image with a smaller amount of attentional resources.

The changes in display mode as described above may be performed in combination where appropriate. Some example cases in which the display mode is changed were described as above with reference to FIG. 9A-1, FIG. 9A-2, FIG. 9B-1, FIG. 9B-2, FIG. 9C-1, FIG. 9C-2, FIG. 10A-1, FIG. 10A-2, FIG. 10B-1, FIG. 10B-2, FIG. 10C-1, and FIG. 10C-2. In those example cases, the display mode is changed based on the degree of change indicating how and how much the display mode is to be changed, which is determined as a result of the determination. For example, the size or thickness of a text or character increases as the degree of change is greater. The brightness gets higher as the degree of change is higher. Regarding the relation of complementary colors, the brightness of the background image may be increased as the degree of change is greater. The level of color saturation gets higher as the degree of change increases. The distance to a virtual image is increased as the degree of change is greater. The rate of flashing gets higher as the degree of change increases.

In the following description, the processes in which the display system 1 changes the display mode of the display image based on at least one of the traveling time, driving environment information, occupant status information, and the display image history are described.

Figure 11:
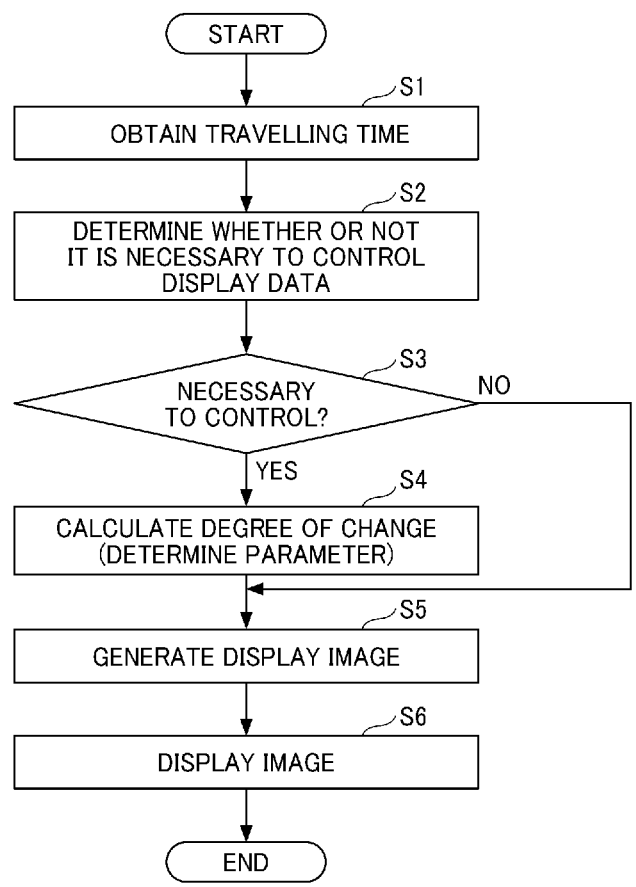
FIG. 11 is a flowchart of the processes in which a display controller changes the display mode of display data based on the traveling time, according to an embodiment of the present disclosure.

FIG. 11 is a flowchart of the processes in which the display controller 20 changes the display mode of the display data based on the traveling time, according to the present embodiment.

Note that the processes in FIG. 11 are executed on a regular basis while the vehicle is traveling.

The traveling time measurement unit 22 accumulates the traveling time based on the vehicle speed obtained from the data input unit 30 (step S1).

The determination unit 26 determines whether or not there is a necessity to change the display mode of the display data based on the traveling time (step S2). For example, it is determined that there is necessity to change the display mode of the display data when the value of traveling time is equal to or greater than a threshold A[s], and it is determined that there is no necessity to change the display mode of the display data when the value of traveling time is less than a threshold B[s]. However, no limitation is intended thereby, and the level of fatigue may be calculated based on the traveling time and determination may be made based on the calculated level of fatigue. It is considered that the level of fatigue of the occupant of the vehicle increases as the traveling time gets longer, and thus the traveling time correlates with the level of fatigue. The threshold A may have a value different from or the same as that of the threshold B.

When it is determined that there is a necessity to change the display mode ("YES" in step S3), the determination unit 26 calculates the degree of change based on the difference between the traveling time and the threshold A (step S4). For example, when the size is to be changed in the display mode, the magnifying power (parameter) of the display image is determined based on the degree of change. The degrees of change are associated with the degrees of magnifying power in advance.

Subsequently, the display image generator 28 generates a display image (step S5). When it is determined that there is no necessity to change the display mode of the display data in the step S3, the display image is generated with the magnifying power of "1." When it is determined that there is a necessity to change the display mode in the step S3, the display image is generated with the magnifying power determined in the step S4.

The image display unit 29 instructs the display device 10 to display the display image generated by the display image generator 28 (step S6).

As a result of the processes in FIG. 11, when it is estimated that the attentional resources of the occupant of the vehicle are low as the traveling time gets longer, the size of the display image is increased so as to be visually recognized with a smaller amount of attentional resources. Accordingly, the occupant of the vehicle can visually recognize the information easily, and the attentional resources to be allocated to the driving operation can be secured easily.

Figure 12:
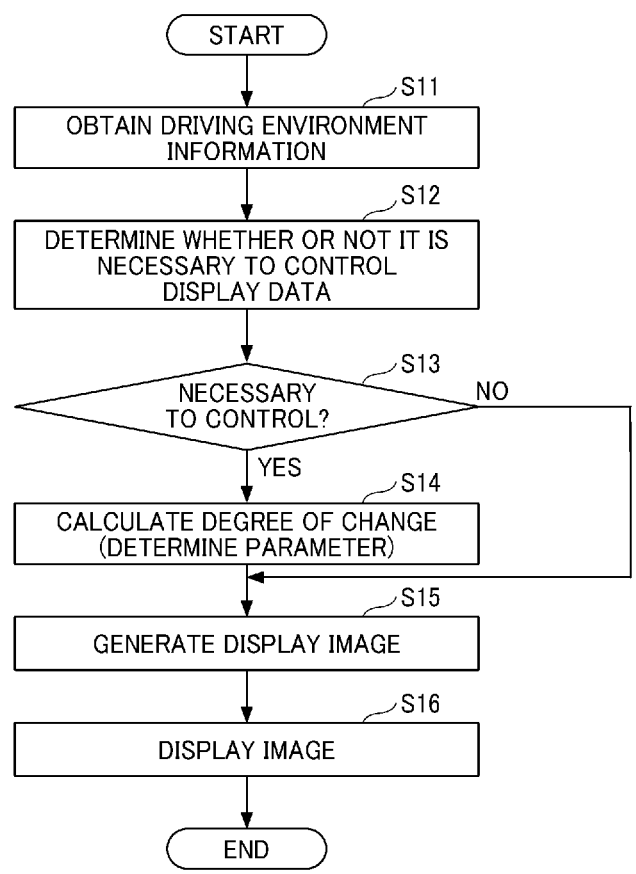
FIG. 12 is a flowchart of the processes in which a display controller changes the display mode of display data based on the driving environment information, according to an embodiment of the present disclosure.

FIG. 12 is a flowchart of the processes in which the display controller 20 changes the display mode of display data based on the driving environment information, according to the present embodiment.

In the description of FIG. 12, the differences from FIG. 11 are described.

In a step S11, the driving environmental information acquisition unit 24 obtains the driving environment information (step S11). The driving environmental information acquisition unit 24 classifies the driving environment information into the first to third groups, and counts the number of times the driving environment information that belong to each group is displayed. Then, the number of times each one of the driving environment information that belongs to the first, second, and the third group is displayed is sent to the determination unit 26.

The determination unit 26 determines whether or not there is a necessity to change the display mode of the display data based on the number of times each one of the driving environment information that belongs to the first, second, and the third group is displayed (step S12). For example, the number of times each one of the driving environment information that belongs to the first, second, and the third group is displayed (display count) is weighted and summed up. As a result, the display count is digitized. It is determined that there is necessity to change the display mode of the display data when the digitized value is equal to or greater than a threshold C, and it is determined that there is no necessity to change the display mode of the display data when the digitized value is less than a threshold D. It is not always necessary for the digitized value to match the level of fatigue. However, the digitized value may be regarded as the level of fatigue, or the value that is proportionate to the digitized value may be regarded as the level of fatigue. The threshold C may have a value different from or the same as that of the threshold D.

When it is determined that there is a necessity to change the display mode ("YES" in step S13), the determination unit 26 calculates the degree of change based on the difference between the digitized driving environment information and the threshold C (step S14). The following steps are equivalent to the steps in FIG. 11.

As a result of the processes in FIG. 12, when it is estimated that the attentional resources of the occupant of the vehicle are low based on the driving environment information, the size of the display image is increased so as to be visually recognized with a smaller amount of attentional resources. Accordingly, the occupant of the vehicle can visually recognize the information easily, and the attentional resources to be allocated to the driving operation can be secured easily.

It is undesired that the number of times each one of the driving environment information that belongs to the first, second, and the third group is displayed simply increases. Preferably, there are some chances for the number of times each one of the driving environment information that belongs to the first, second, and the third group is displayed to decrease. For example, when the driving environment information that belongs to the second and third groups is not output for certain length of time, the number of times the driving environment information that belongs to the second and third groups is output is counted down at prescribed time intervals (the number of times the driving environment information that belongs to the first group is displayed at all times is displayed is not counted down because the driving environment information that belongs to the first group is displayed at all times). Due to such a configuration, the number of counts is decreased when the driving environment information is output due to simple carelessness instead of due to tiredness or fatigue. Accordingly, the display mode of the display data can be prevented from being changed and remaining in the changed display mode. On the other hand, the tiredness or fatigue is accumulated over time. As a result, the number of times the driving environment information that belongs to the second and third groups is output increases. Accordingly, a display image that can be visually recognized with a smaller amount of attentional resources can be displayed.

As described above with reference to FIG. 12, the driving environment information on which whether or not the display mode is to be changed is determined is based is equivalent to the driving environment information to be displayed. For example, when it is determined that the vehicle may abnormally get close to an object, a character or an icon that prompts the driver to press down the brake pedal is displayed, and the way of presenting the image of such a character or icon is changed.

However, there are some cases in which the display device 10 displays the vehicle speed, at least one item of vehicle-related information, or a message derived from the occupant status information or the occupant status information as it is in addition to the driving environment information, and the display device 10 may display the display data other than the driving environment information may be displayed at the same time as the driving environment information.

Figure 13A:
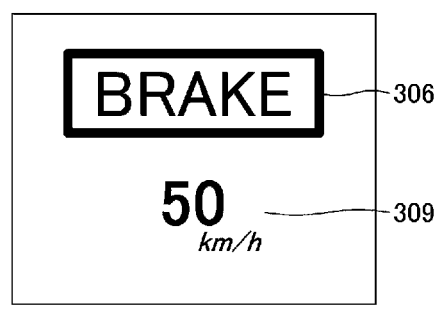
FIG. 13A and FIG. 13B are diagrams each illustrating the display data other than driving environment information, which is displayed by a display device at the same time as the driving environment information, according to an embodiment of the present disclosure.
Figure 13B:
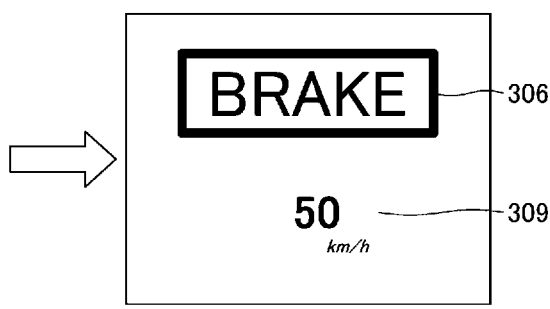

FIG. 13A and FIG. 13B are diagrams each illustrating the display data other than the driving environment information, which is displayed by the display device 10 at the same time as the driving environment information, according to the present embodiment.

In FIG. 13A, a message 306 saying "BRAKE," which indicates one of the desirable operations performed by the occupant of the vehicle, is displayed as the driving environment information, and a vehicle speed 309 is displayed as an example of the display data other than the driving environment information. In such a configuration, the display mode of the display data other than the driving environment information may be changed to a display mode where information needs to be visually recognized with a greater amount of attentional resources (such that the stimulative properties and characteristics are reduced). More specifically, as illustrated in FIG. 13B, the vehicle speed 309 is made less noticeable. There are several methods to make the display data less noticeable. For example, the characters (texts) may be downsized, or the thickness of the characters (texts) may be reduced. Alternatively, the brightness may be reduced, or the color of the background of the image of contents of data may be changed to a color other than the complementary color of the color of the image of contents of data. Alternatively, the level of color saturation may be decreased, or the distance to a virtual image may be shortened.

By so doing, the degree of stimulation of the driving environment information in the message 306 is relatively increased. Accordingly, the occupant of the vehicle can visually recognize the message 306 with a smaller amount of attentional resources.

In such a configuration, it is not necessary for the display mode of the message 306, which is the driving environment information obtained by the driving environmental information acquisition unit 24, to be changed, or the display mode of the message 306 may be changed to a display mode where information can visually be recognized with a smaller amount of attentional resources. Alternatively, the image of the vehicle speed 309, which is an example of the display data other than the driving environment information, may be erased.

Note also that the control as described above with reference to FIG. 13A and FIG. 13B may be implemented without counting the number of times the driving environment information that belongs to the second and third groups is output. When the number of times the driving environment information that belongs to the second and third groups is output is not counted, it becomes difficult to perform control based on the degree of change. In such cases, the display mode of the display data other than the driving environment information is changed to a predetermined display mode. Moreover, in such cases, the display mode may be changed without a lapse of time (for example, the accumulation of tiredness or fatigue) unlike the cases in which determination is made based on the traveling time or the number of times the driving environment information is obtained.

Figure 14:
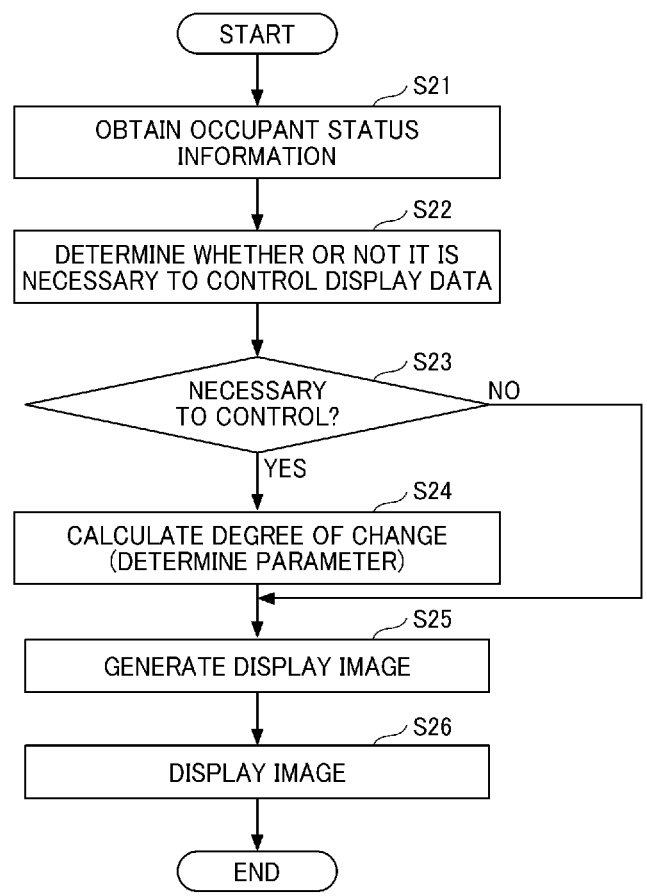
FIG. 14 is a flowchart of the processes in which a display controller changes the display mode of display data based on the occupant status information, according to an embodiment of the present disclosure.

FIG. 14 is a flowchart of the processes in which the display controller 20 changes the display mode of the display data based on the occupant status information, according to the present embodiment.

In the description of FIG. 14, the differences from FIG. 11 are described.

In step S21, the occupant status information acquisition unit 23 obtains the occupant status information (S21). The occupant status information acquisition unit 23 converts the obtained occupant status information into the amount of decrement in attentional resources, and sends the obtained the amount of decrement in attentional resources to the determination unit 26.

The determination unit 26 determines whether or not there is a necessity to change the display mode of the display data based on the amount of decrement in attentional resources (step S22). For example, it is determined that there is necessity to change the display mode of the display data when the amount of decrement in attentional resources is equal to or greater than a threshold E, and it is determined that there is no necessity to change the display mode of the display data when the amount of decrement in attentional resources is less than a threshold F.

However, no limitation is intended thereby, and the level of fatigue may be calculated and determination may be made based on the calculated level of fatigue. For example, the amount of decrement in attentional resources or the value that is proportionate to the amount of decrement in attentional resources is obtained as the level of fatigue. The threshold E may have a value different from or the same as that of the threshold F.

When it is determined that there is a necessity to change the display mode ("YES" in step S23), the determination unit 26 calculates the degree of change based on the difference between the amount of decrement in attentional resources and the threshold E (step S24). The following steps are equivalent to the steps in FIG. 11.

As a result of the processes in FIG. 14, when it is estimated that the attentional resources of the occupant of the vehicle are low based on occupant status information, the size of the display image is increased so as to be visually recognized with a smaller amount of attentional resources. Accordingly, the occupant of the vehicle can visually recognize the information easily, and the attentional resources to be allocated to the driving operation can be secured easily.

In the processes as described above with reference to FIG. 14, even when the attentional resources are consumed on a temporary basis due to, for example, the traffic congestion or the existence of other vehicles, the amount of reduction in attentional-resources consumption decreases when a factor in consuming the attentional resources is resolved. Due to such a configuration, the display mode may be prevented from being changed and remaining in the changed display mode. It is considered that a factor that tends to be accumulated such as the level of alertness is tiredness or fatigue. In such cases where the factor is considered to be tiredness or fatigue, the amount of reduction in attentional-resources consumption tends to increase, and the display mode may be changed and maintained in the changed display mode.

Figure 15:
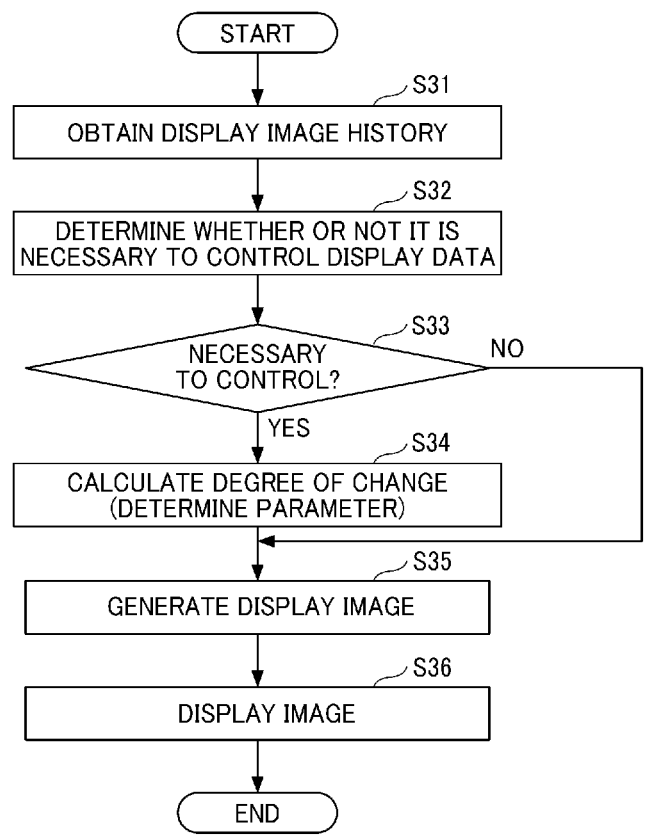
FIG. 15 is a flowchart of the processes in which a display controller changes the display mode of display data based on the display image history, according to an embodiment of the present disclosure.

FIG. 15 is a flowchart of the processes in which the display controller 20 changes the display mode of the display data based on the display image history, according to the present embodiment.

In the description of FIG. 15, the differences from FIG. 11 are described.

In step S31, the display image history storage unit 25 stores the display image history (step S31). The display image history storage unit 25 converts the display image history into the amount of attentional-resources consumption, and sends the obtained the amount of attentional-resources consumption to the determination unit 26.

The determination unit 26 determines whether or not there is a necessity to change the display mode of the display data based on the amount of attentional-resources consumption (step S32). For example, it is determined that there is necessity to change the display mode of the display data when the amount of attentional-resources consumption is equal to or greater than a threshold G, and it is determined that there is no necessity to change the display mode of the display data when the amount of attentional-resources consumption is less than a threshold H. However, no limitation is intended thereby, and the level of fatigue may be calculated and determination may be made based on the calculated level of fatigue. For example, the amount of attentional-resources consumption or the value that is proportionate to the amount of attentional-resources consumption is obtained as the level of fatigue. The threshold G may have a value different from or the same as that of the threshold H.

When it is determined that there is a necessity to change the display mode ("YES" in step S33), the determination unit 26 calculates the degree of change based on the difference between the amount of attentional-resources consumption and the threshold G (step S34). The following steps are equivalent to the steps in FIG. 11.

As a result of the processes in FIG. 15, when it is estimated that the attentional resources of the occupant of the vehicle are low based on the display image history, the size of the display image is increased so as to be visually recognized with a smaller amount of attentional resources. Accordingly, the occupant of the vehicle can visually recognize the information easily, and the attentional resources to be allocated to the driving operation can be secured easily. It is considered that the level of fatigue of the occupant of the vehicle increases as the occupant of the vehicle visually recognize more display images. For this reason, the display mode may be changed to a display mode where information can visually be recognized with a smaller amount of attentional resources as the amount of display image history increases.

Figure 16:
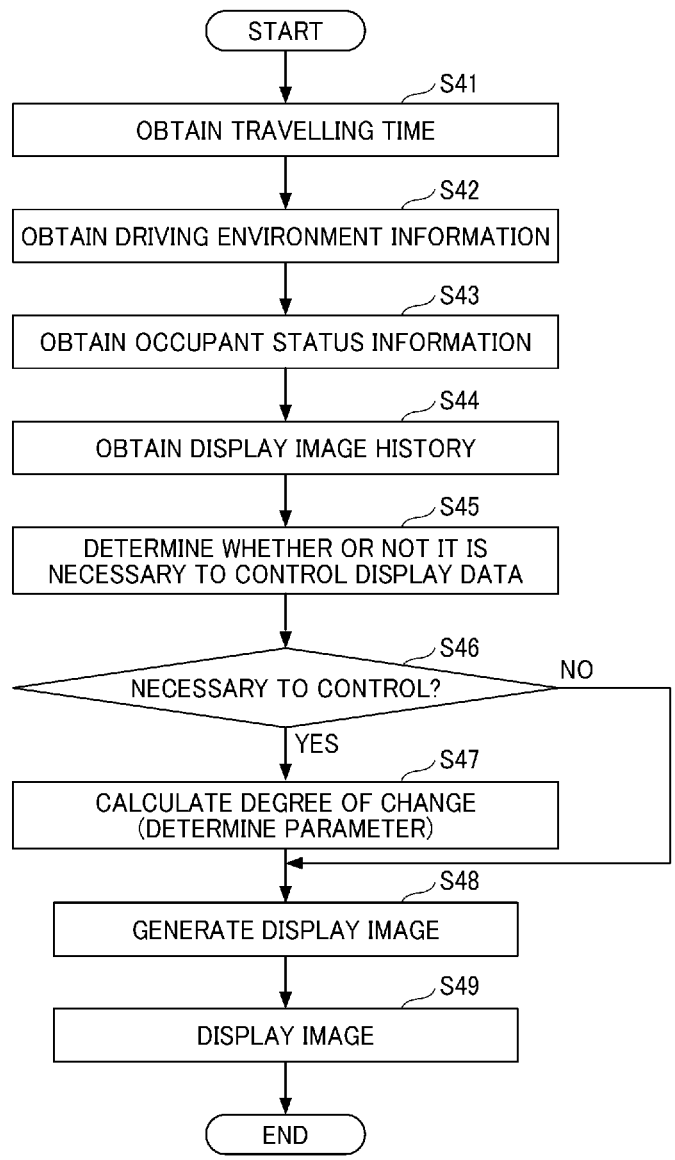
FIG. 16 is a flowchart of the processes in which a display controller changes the display mode of display data based on the traveling time, driving environment information, occupant status information, and the display image history, according to an embodiment of the present disclosure.

FIG. 16 is a flowchart of the processes in which the display controller 20 changes the display mode of display data based on the traveling time, driving environment information, occupant status information, and the display image history, according to the present embodiment.

In the description of FIG. 16, the differences from FIG. 11 are described.

In steps S41 to S44, the traveling time measurement unit 22 obtains the traveling time, and the driving environmental information acquisition unit 24 obtains the driving environment information. Moreover, the occupant status information acquisition unit 23 obtains the occupant status information, and the display image history storage unit 25 stores the display image history (steps S41 to S44). The traveling time, the number of times each one of the driving environment information that belongs to the first, second, and the third group is displayed based on the driving environment information, the amount of reduction in attentional-resources consumption based on the occupant status information, and the amount of attentional-resources consumption based on the display image history are sent to the determination unit 26.

The determination unit 26 determines whether or not there is a necessity to change the display mode of the display data based on all the received information (step S45). For example, firstly, each of the traveling time, the number of times each one of the driving environment information that belongs to the first, second, and the third group is displayed (display count), the amount of reduction in attentional-resources consumption based on the occupant status information, and the amount of attentional-resources consumption based on the display image history is weighted and digitized. Then, it is determined that there is necessity to change the display mode of the display data when one of the digitized values is equal to or greater than a threshold I, and it is determined that there is no necessity to change the display mode of the display data when one of the digitized values is less than a threshold J. However, no limitation is intended thereby, and the level of fatigue may be calculated and determination may be made based on the calculated level of fatigue. The threshold I may have a value different from or the same as that of the threshold J.

When it is determined that there is a necessity to change the display mode ("YES" in step S46), the determination unit 26 calculates the degree of change based on the difference between the digitized value and the threshold I (step S47). The following steps are equivalent to the corresponding steps in FIG. 11.

When it is estimated as a result of the processes in FIG. 16 that the attentional resources of the occupant of the vehicle are low in view of all the factors including the traveling time, the driving environment information, the occupant status information, and the display image history, the size of the display image is increased so as to be visually recognized with a smaller amount of attentional resources. Accordingly, the occupant of the vehicle can visually recognize the information easily, and the attentional resources to be allocated to the driving operation can be secured easily.

Figure 17:
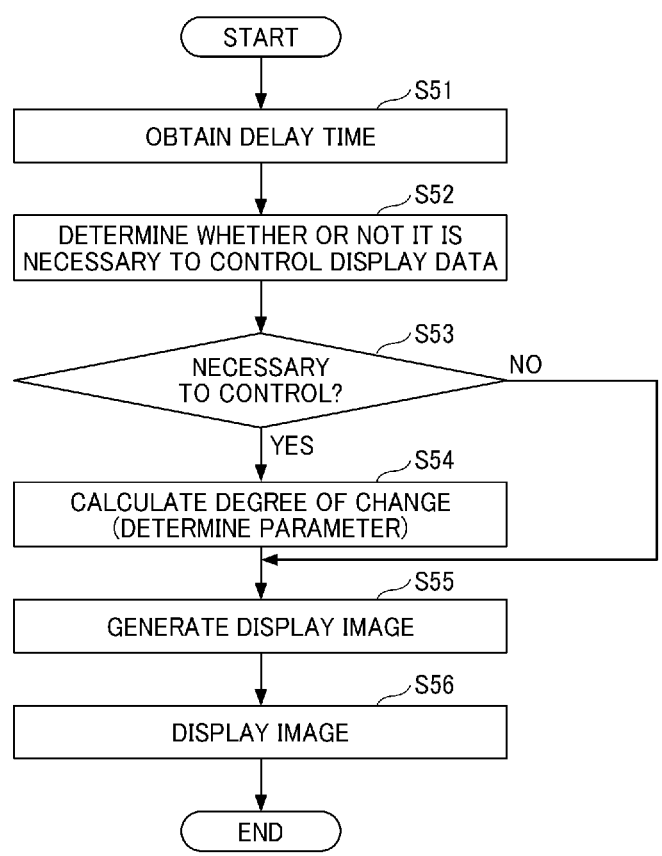
FIG. 17 is a flowchart of the processes in which a display controller changes the display mode of display data based on the delay time between the timing at which recommendable operation is obtained and the timing at which the information about the operation specified by the recommendable operation is input, according to an embodiment of the present disclosure.

FIG. 17 is a flowchart of the processes in which the display controller 20 changes the display mode of the display data based on the delay time between the timing at which the recommendable operation is obtained and the timing at which the information about the operation specified by the recommendable operation is input, according to the present embodiment.

In the description of FIG. 17, the differences from FIG. 11 are described.

Firstly, the operation feedback acquisition unit 27 obtains the delay time (step S51). Then, the operational feedback acquisition unit 27 sends the delay time to the determination unit 26.

The determination unit 26 determines whether or not there is a necessity to change the display mode of the display data based on the received delay time (step S52). For example, it is determined that there is necessity to change the display mode of the display data when the value of the delay time is equal to or greater than a threshold K, it is determined that there is no necessity to change the display mode of the display data when the value of the delay time is less than a threshold L. However, no limitation is intended thereby, and the level of fatigue may be calculated and determination may be made based on the calculated level of fatigue. For example, the value of the delay time or the value that is proportionate to the value of the delay time is obtained as the level of fatigue. The threshold K may have a value different from or the same as that of the threshold L.

When it is determined that there is a necessity to change the display mode ("YES" in step S53), the determination unit 26 calculates the degree of change based on the difference between the delay time and the threshold K (step S54). The following steps are equivalent to the corresponding steps in FIG. 11.

As a result of the processes in FIG. 17, when it is estimated that the attentional resources of the occupant of the vehicle are low based on the delay time, the size of the display image is increased so as to be visually recognized with a smaller amount of attentional resources. Accordingly, the occupant of the vehicle can visually recognize the information easily, and the attentional resources to be allocated to the driving operation can be secured easily.

When the delay time is shortened as, for example, the occupant of the vehicle focuses on the driving, the display mode can be prevented from being changed and remaining in the changed display mode. When the delay time is extended due to the fatigue or the like, the amount of reduction in attentional-resources consumption tends to increase, and the display mode may be changed and maintained in the changed display mode.

As described above, the display device 10 according to the present embodiment determines the display mode of the information so as to be visually recognized with a smaller amount of attentional resources depending on the input data that may affect the attentional resources of the occupant of the vehicle. Accordingly, the occupant of the vehicle can visually recognize the information easily, and the attentional resources to be allocated to the driving operation can be secured easily. Moreover, as the information can be visually recognized with a smaller amount of attentional resources, the accumulation of fatigue can be eased.

Figure 18:
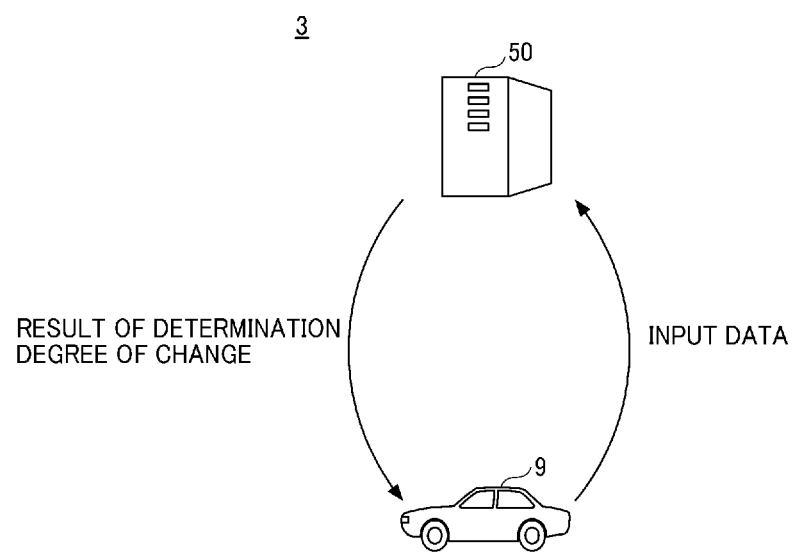
FIG. 18 is a diagram illustrating a schematic configuration of an information processing system that includes a server and a vehicle, according to an embodiment of the present disclosure.

The processes according to the present embodiment are implemented by the vehicle-installed system 2 provided for the vehicle. As illustrated in FIG. 18, the processes according to the present embodiment can be applied to an information processing system of server-client type.

FIG. 18 is a diagram illustrating a schematic configuration of an information processing system 3 that includes a server 50 and the vehicle 9, according to the present embodiment.

The vehicle 9 may include a plurality of vehicles. Each of the vehicles 9 serves as a probe car, and sends some of or the entirety of the input data, which is input from the data input unit 30 of the vehicle 9, to the server 50. The server 50 has the functions of the traveling time measurement unit 22, the occupant status information acquisition unit 23, the driving environmental information acquisition unit 24, and the determination unit 26, and sends the result of the determination and the degree of change to the vehicle 9.

For example, when traffic congestion is taking place at a long distance or the weather is turning bad, the server 50 shares such information with the probe car. When it is determined that the attentional resources tend to be consumed in the path to the destination, the display controller 20 provided for a vehicle displays the display image, in advance, in a display mode where relatively less attentional resources are consumed. In other words, a less stimulating display image is displayed. When the amount of attentional-resources consumption is predicted as described above, the display mode may be changed in advance to save the attentional resources.

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

For example, the information to be displayed by the display device 10 may be determined based on the input data. For example, the traveling time as it is, the occupant status information, and the display image history may be displayed.

For example, the virtual image I may be displayed upon performing camera-shake correction thereon, or the virtual image I may be displayed along the traffic lane as in the augmented reality (AR).

The display device 10 may be, for example, a liquid crystal display. The housing of the display controller 20 may be separate from the housing of the display device 10. For example, the display controller 20 and the display device 10 may independently be distributed. For example, a smartphone may be used as the display controller 20, and information may be displayed on the display that is built into the smartphone. Alternatively, a virtual image may be displayed on a combiner (light transmission member).

Each one of the traveling time measurement unit 22, the occupant status information acquisition unit 23, the driving environmental information acquisition unit 24, and the display image history storage unit 25 is an example of an information acquisition unit. The display image generator 28 is an example of a display-image generation unit, and the display controller 20 is an example of a display controller.

This patent application is based on and claims priority to Japanese Patent Application No. 2019-003693, filed on Jan. 11, 2019, in the Japan Patent Office, the entire disclosures of which is hereby incorporated by reference herein.

REFERENCE SINGS LIST

1 Display system
2 Vehicle-installed system
9 Vehicle
10 Display device
11 Car navigation system
20 Display controller
30 Data input unit

The invention claimed is:

1. A display controller, comprising:
circuitry configured to
obtain input data of attentional resources of an occupant of a mobile object; and
generate, in a mode determined based on the input data, a display image to be displayed by a display device provided for the mobile object,
wherein the circuitry is further configured to obtain, as the input data, occupant status information indicating a state of the occupant of the mobile object, and generate, in a mode determined based on the obtained occupant status information, the display image to be displayed by the display device,
wherein the circuitry is further configured to:
obtain, as the input data, driving environment information indicating driving environment of the mobile object,
generate, in a mode determined based on the obtained driving environment information, the display image indicating the obtained driving environment information,
generate, in the mode determined based on the driving environment information, the display image to be displayed by the display device together with the driving environment information in addition to the driving environment information, and
change the mode such that the driving environment information is displayed with increased stimulative properties.

2. The display controller according to claim 1, wherein the circuitry is further configured to obtain a traveling time of the mobile object as the input data, and generate, in a mode determined based on the obtained traveling time, the display image to be displayed by the display device.

3. The display controller according to claim 1, wherein the circuitry is further configured to:
obtain and store, as the input data, display image history indicating a display record of the display image to be displayed by the display device, and
generate, in a mode determined based on the display image history, the display image to be displayed by the display device.

4. The display controller according to claim 3, wherein the circuitry is further configured to determine a mode of the display image to be displayed by the display device, based on a level of fatigue of the occupant converted from the input data including at least one of a traveling time of the mobile object, the occupant status information indicating the state of the occupant of the mobile object, the driving environment information indicating the driving environment of the mobile object, and the display image history.

5. The display controller according to claim 1, wherein the circuitry is further configured to generate the display image to be displayed by the display device, in a mode determined based on length of delay time between a timing at which a recommendable operation to be performed by the occupant of the mobile object is displayed by the display device and a timing at which the recommendable operation performed by the occupant of the mobile object is detected.

6. The display controller according to claim 1, wherein the occupant status information indicating the state of the occupant of the mobile object is at least one of electrocardiogram information, a heart rate, blood pressure, body temperature, a pulse, a respiration rate, an amount of perspiration, an arousal level, a brain wave, and a myoelectric potential.

7. The display controller according to claim 1, wherein the driving environment information indicating the driving environment of the mobile object is at least one of a status of various kinds of controls based on information detected by various kinds of sensors including a light detection and ranging device and a camera, an operation to be performed by the occupant of the mobile object, traffic congestion information, information about traffic accident, and weather information.

8. The display controller according to claim 1,
wherein the mobile object is a vehicle, and
wherein the information to be displayed by the display device comprises:
vehicle-related information obtainable from the vehicle including vehicle speed, remaining fuel, a shift-lever position, total mileage, sectional mileage, a state of a direction indicator, and water temperature;
the driving environment information including a status of various kinds of controls based on information detected by various kinds of sensors including a light detection and ranging device and a camera, an operation to be performed by an occupant of the vehicle, traffic congestion information, information about traffic accident, and weather information; and
information about a physical and mental state of the occupant of the vehicle, including electrocardiogram information, a heart rate, blood pressure, body temperature, a pulse, a respiration rate, an amount of perspiration, an arousal level, an electrical brain wave, and a myoelectric potential of the occupant of the vehicle, or information derived from the electrocardiogram information, the heart rate, the blood pressure, the body temperature, the pulse, the respiration rate, the amount of perspiration, the arousal level, the electrical brain wave, and the myoelectric potential of the occupant of the vehicle.

9. A display device, comprising:
display circuitry configured to:
   obtain the display image from the display controller according to claim 1, and
   project the obtained display image onto a front windshield to cause a virtual image of the display image to be visually recognized by the occupant of the mobile object ahead of the front windshield.

10. The display device according to claim 9, wherein the display image is formed by a laser beam, and the display image formed by the laser beam is projected onto the front windshield.

11. A display system, comprising:
the display controller according to claim 1; and
a display device configured to obtain the display image from the display controller and to project the obtained display image onto a front windshield, to generate, ahead of the front windshield, a virtual image of the display image to be visually recognized by the occupant of the mobile object.

12. A mobile object comprising the display system according to claim 11.

13. The display controller according to claim 1, wherein:
the change of the mode increases the stimulative properties by changing a size of information being displayed.

14. The display controller according to claim 13, wherein:
the change of the mode increases the stimulative properties by changing a size of a speed of the mobile object being displayed.

15. A method of generating an image, using a display controller that causes a display device provided for a mobile object to display information, the method comprising:
   obtaining input data influencing attentional resources of an occupant of the mobile object; and
   generating, in a mode determined based on the input data, a display image to be displayed on the display device provided for the mobile object,
the method further comprising:
   obtaining, as the input data, occupant status information indicating a state of the occupant of the mobile object, and generate, in a mode determined based on the obtained occupant status information, the display image to be displayed by the display device, and driving environment information indicating driving environment of the mobile object,
   generating, in a mode determined based on the obtained driving environment information, the display image indicating the obtained driving environment information,
   generating, in the mode determined based on the driving environment information, the display image to be displayed by the display device together with the driving environment information in addition to the driving environment information, and
   changing the mode such that the driving environment information is displayed with increased stimulative properties.

16. A non-transitory computer-readable medium storing a computer-readable program for controlling a computer to perform the method of claim 15.

17. The method according to claim 15, wherein:
the changing of the mode increases the stimulative properties by changing a size of information being displayed.

18. The method according to claim 17, wherein:
the changing of the mode increases the stimulative properties by changing a size of a speed of the mobile object being displayed.

* * * * *